(12) United States Patent
Mastrogiovanni

(10) Patent No.: US 10,127,698 B2
(45) Date of Patent: Nov. 13, 2018

(54) METHOD, APPARATUS AND SYSTEM FOR FINANCIAL PLANNING INCORPORATING CALCULATED HEALTH COSTS BASED ON ACTUAL CLAIMS AND THE ACTUAL COST THEREOF

(71) Applicant: HEALTHVIEW SERVICES, INC., Danvers, MA (US)

(72) Inventor: Renato Mastrogiovanni, Topsfield, MA (US)

(73) Assignee: Healthview Services, Inc., Danvers, MA (US)

( * ) Notice: Subject to any disclaimer, the term of this patent is extended or adjusted under 35 U.S.C. 154(b) by 0 days.

(21) Appl. No.: 13/815,640

(22) Filed: Mar. 13, 2013

(65) Prior Publication Data

US 2013/0304618 A1 Nov. 14, 2013

Related U.S. Application Data

(60) Provisional application No. 61/688,231, filed on May 10, 2012.

(51) Int. Cl.
*G06Q 40/00* (2012.01)
*G06T 11/60* (2006.01)
*A61B 3/10* (2006.01)

(52) U.S. Cl.
CPC .............. *G06T 11/60* (2013.01); *A61B 3/102* (2013.01); *G06Q 40/00* (2013.01)

(58) Field of Classification Search
CPC .... G06Q 50/22; G06Q 10/0635; G06Q 40/00; G06Q 40/08; G06Q 40/02; G06Q 40/06; A61B 3/102; G06T 11/60
See application file for complete search history.

(56) References Cited

U.S. PATENT DOCUMENTS

| | | | |
|---|---|---|---|
| 5,987,433 A | 11/1999 | Crapo | |
| 6,643,600 B2 * | 11/2003 | Yanosik, Jr. | ......... G05B 19/406 700/28 |
| 7,330,818 B1 | 2/2008 | Ladocsi et al. | |
| 7,698,155 B1 * | 4/2010 | Prasad | .................. G06F 19/328 705/3 |

(Continued)

FOREIGN PATENT DOCUMENTS

WO WO 01/075742 * 10/2001
WO WO-2007014307 A2 * 2/2007

OTHER PUBLICATIONS

Shaughnessey et al.: Overview of risk adjustment and outcome measures for home health agency QBQI Reports: Highlights of current approaches and ouline of planned enhancements, Sep. 2002, Center for Health Services Research, UCHSC, Denver, CO, pp. 1-17.*

(Continued)

*Primary Examiner* — Bijendra K Shrestha
(74) *Attorney, Agent, or Firm* — Pepper Hamilton LLP

(57) ABSTRACT

A financial management tool that includes calculated health care costs and health-based longevity to provide information to retirees to be able to calculate the amount of money that needs to be saved to cover retirement expenditures is provided with actual claims and actual related cost data from a database to increase the cost projection reliability of the tool.

10 Claims, 14 Drawing Sheets

(56) References Cited

U.S. PATENT DOCUMENTS

| | | | |
|---|---|---|---|
| 7,702,527 B1* | 4/2010 | Kron | G06Q 40/08 705/2 |
| 7,711,619 B2* | 5/2010 | Merton et al. | 705/35 |
| 8,306,832 B2* | 11/2012 | Shrivastava | G06Q 40/08 705/4 |
| 8,630,871 B2* | 1/2014 | Rastogi | G06Q 30/018 705/2 |
| 2005/0202390 A1* | 9/2005 | Allen | G09B 7/00 434/353 |
| 2005/0278196 A1* | 12/2005 | Potarazu | G06Q 10/10 705/2 |
| 2007/0027727 A1* | 2/2007 | Cochrane | G06F 19/328 705/4 |
| 2007/0250427 A1* | 10/2007 | Robinson | G06Q 40/00 705/36 R |
| 2008/0010086 A1* | 1/2008 | Skelly | G06F 19/328 705/2 |
| 2008/0027753 A1* | 1/2008 | Dean | G06F 19/328 705/2 |
| 2008/0133272 A1* | 6/2008 | Marshall | G06F 19/322 705/3 |
| 2009/0192827 A1* | 7/2009 | Andersen | G06Q 40/08 705/4 |
| 2009/0319440 A1 | 12/2009 | Montgomery et al. | |
| 2010/0250277 A1* | 9/2010 | Kuriyan | G06F 19/328 705/2 |
| 2011/0166978 A1 | 7/2011 | Mastrogiovanni | |
| 2012/0173398 A1* | 7/2012 | Sjodin | G06Q 40/00 705/35 |
| 2013/0144642 A1* | 6/2013 | Bessette | G06F 19/327 705/2 |

OTHER PUBLICATIONS conceptstew.co.uk: The Importance of n (sample size) in Statistics: Oct. 7, 2011 (Web Archives), pp. 1-2.*

Medpac: Hospital Acute Inpatient Services Payment System, Payment Basics, Oct. 2009, pp. 1-5.*

Wright, C.: Research Methodology: A Guide to Sampling & Statistical Reliability, Jul. 2009, Research Sandwell, Technical Note 5, pp. 1-5.*

Kipp et al.: Health Insurance Underwriting Cycle: Effect on Health Plan Premium and Profitability, Apr. 10, 2003, Milliman USA, pp. 1-43.*

Damler et al.: ACA Premium Impact—Variability of Individual Market Premium Rate Changes, Mar. 2012, Milliman, Inc., pp. 1-15.*

Bruton et al.: Reliability: What is it, and how is it measured? Feb. 2008, Physiotherapy, vol. 86/No. 2, pp. 94-99.*

Damler et al.: ACA Premium Impact—Variability of Individual Market Premium Rate Changes, Mar. 2012, Milliman, Inc., pp. 1-15. (Year: 2012).*

American Hospital Association (AHA): When I'm 64: How Boomers Will Change Health Care, May 2007, pp. 1-24. (Year: 2007).*

Fronstin et al.: Retiree Health Benefits: Savings Needed to Fund Health Care in Retirement, Feb. 2003, Employee Benefit Research Institute (EBRI), Issue 254, pp. 1-28. (Year: 2003).*

* cited by examiner

Example 1
How Algorithms Are Applied

To show calculation steps simply hover your mouse over any amount in blue.

| | Medical (Individual) | Rx (Individual) | Medical (Emp-Based) | Rx (Emp-Based) | Dental | Docs/Tests Hosp | Rx | Dental | All Hearing | Vision |
|---|---|---|---|---|---|---|---|---|---|---|
| 45 year-old male in Alabama Has poorly-managed Type 2 diabetes diagnosed within last year .. Full Detail >> Full Detail (ind covg) >> | Age 45 (2013) | $4,131.72 | $1,328.69 | $1,032.93 | $332.17 | $213.36 | $1,173.54 | $1,039.13 | $94.72 | $1.10 | $206.86 |
| | Age 65 (2033) | $52,450.78 | $13,161.03 | $3,997.11 | $1,285.40 | $570.43 | $18,232.43 | $9,373.82 | $324.12 | $6.59 | $961.85 |
| | Age 71 (2039) (death by Type 2 Diabetes) | $109,237.50 | $24,099.66 | $5,998.58 | $1,929.04 | $76 | | | | | 74.15 |
| 45 year-old male in Alabama Has well-managed Type 2 diabetes diagnosed within last year .. Full Detail >> Full Detail (ind covg) >>0 | Age 45 (2013) | $4,131.72 | $1,328.69 | $1,032.93 | $332.17 | $21 | | | | | 06.86 |
| | Age 65 (2033) | $52,460.78 | $13,161.03 | $3,997.11 | $1,285.40 | $57 | | | | | 61.85 |
| | Age 80 (2048) (death by Type 2 Diabetes) | $284,959.20 | $56,298.04 | $11,028.15 | $3,546.46 | $1,192.69 | $51,027.44 | $19,124.26 | $689.78 | $23.39 | $3,105.65 |

Callout (on $18,232.43):
- Base Amount = $294.29 based on Diabetes Type2 managed poorly, diagnosed 0-1 years ago.
- Trended forward 21 years at 7.00% = > $1,218.52.
- Apply age/gender factor af 971.610% = > $11,839.24
- Apply disease management factor of 154.000% = > $18,232.43.
- Apply years since diagnosis factor of 100.000% = > $18,232.43.

*Fig. 12*

METHOD, APPARATUS AND SYSTEM FOR FINANCIAL PLANNING INCORPORATING CALCULATED HEALTH COSTS BASED ON ACTUAL CLAIMS AND THE ACTUAL COST THEREOF

FIELD OF THE INVENTION

This invention relates to financial planning tools and more particularly to the incorporation of calculated health costs based on actual claims and the actual costs of resolving these claims.

BACKGROUND OF THE INVENTION

Since healthcare is one of the most expensive cost items that individuals face in retirement it is important to be aware of these costs and to be able to project them with a high degree of certainty. Retirement studies have shown that healthcare costs are approximately 33% of all expenditures of individuals over the age of 60. These healthcare costs vary with respect to the state in which one will live in retirement, the individual's expected income level and other factors that are related to the individual. It is therefore important during the prediction of how to allocate resources in retirement that one does not just rely on a verbal survey to calculate what is required in retirement but rather than picking an arbitrary healthcare cost number there is a necessity for establishing healthcare cost numbers that more accurately reflect what will happen to the particular individual in retirement based on age, gender, health conditions, expected state of residence and income since Medicare is means tested.

As will be seen the subject invention relies on actual claims data and actual costs for resolving these claims upon which and healthcare costs as projected. This means that projections are based on actual claims data, meaning data that reflects actual claims and data that reflects the actual cost of resolving the claims.

It is noted that there are many companies in the United States that attempt to project health costs by conducting surveys with consumers, asking their opinions about what they plan to do in retirement while taking into account their own personal healthcare expenses.

The companies which conduct these surveys utilize sample sizes on the order of 1,000 to 2,000 people and they are almost instantaneously out-of-date because the information is pertinent to the specific period of time at which it was collected. The result historically is that the information regarding retirement planning from companies in the healthcare space are based on this survey-based data.

Typically in these surveys a sample of individuals are surveyed who typically are people who will be retiring in the next 5 to 10 years. Financial planning institutions collect the attitudes of the surveyed individuals in order to form the foundation from which the institution can project costs. It is noted that these surveys are based on what individuals perceive and are not based on anything having to do with actual behavior or actual costs. Typically the surveys are conducted on-line with a random set of on-line individuals, typically over the age of 55. The individuals are asked a set of questions, with the answers collected and published to be able to project healthcare cost estimates or averages from the survey-based information.

There is another survey-based population in which surveys are conducted by the Center for Disease Control (CDC). These surveys have survey populations based on groups of people having particular chronic diseases such as cancer or cardiovascular disease. The data available from the CDC is a combination of observations based on health conditions appended to the reported attitudes of the people surveyed. The data from the CDC is valuable because the CDC knows about the various chronic conditions so that the CDC can make generalizations about the attitudes and behaviors of selected populations.

From the point of view of a statistician and a notion of valid sample sizes, when one wishes to give financial advice to an individual regarding his or her healthcare cost and try to project into the future what the individual's healthcare costs will be it is absolutely imperative that one has a valid sample size that reflects the individual's profile. Thus, for example, for a man who is age 50 and has type II diabetes and who plans to live in Florida in his retirement, when one tries to assemble data related to these combinations together with the relevant populations for each of these profiles the available sample size is miniscule.

Thus, in order to validate the outcome for that individual given the combinations in his or her profile one needs to have a valid cell behind the projections of actual behavior. No such cell currently exists.

In the United States there is currently one independent calculation of actuarial data in which claims data is collected across all of the health insurers. That data of for instance involves 50 million records per year to populate a very extensive database from which one can derive algorithms to actuarially project healthcare costs that are statistically reliable for an individual for a wide number of these combinations of circumstances. If one could obtain claims data and the real cost of resolving these claims one could form a very solid and accurate, precise estimate of what the individual's healthcare costs will be on an annual basis.

Thus, in the past what surveys exist are based on 1,000 to 4,000 people per year and one cannot analyze that population down to the finite level required for statistically reliable healthcare data for an individual.

One healthcare related financial management tool for which accurate healthcare cost data is required is described in U.S. patent application Ser. No. 12/655,591 filed Jan. 4, 2010, incorporated herein by reference. It is to this financial tool that it is critically important to bring statistically accurate and viable healthcare costs and statistics.

Up to the present time there has been no complete database for financial healthcare tools that are statistically robust enough to provide meaningful financial advice, primarily because what tools that do exist do not incorporate actual claims data and actual costs of resolving these claims.

By way of further background, financial services available from a large number of companies include comprehensive planning tools that aid individuals in planning for retirement. These comprehensive planning tools such as those available from Zywave's Naviplan provide an individual with ways of planning for the individual's retirement based on the individual's personal financial profile. Typically these comprehensive planning tools take into account contributing factors, such as fixed and variable living expenses such as mortgage, food, utilities, clothing, vacation expenses, charity donations, and taxes. Typically these tools specify a retirement date and project available funds by taking into account various income sources as well as expenses throughout the retirement period.

These comprehensive tools may factor in retirement income generated from sources such as savings, Social Security, a pension, veterans benefits as well as employment during retirement.

All of these comprehensive tools project available cash or income while making adjustments for variables such as inflation and the rate of return, allowing an investment counselor to determine the financial status of their client The problem with such comprehensive planning tools is that they fail to take into account out of pocket health care costs and actuarially based expected longevity derived from a personal health profile for each individual. Up until the present time, there has been no way of calculating an investors future out of pocket health care costs based on a customized personal medical profile and expected lifespan. As medical expenses will be the single largest expense Americans will face in retirement, it is critically important that financial planners have an accurate and consistent means of incorporating health care expenses and life span into the retirement planning process. Moreover, traditional retirement planning tools do not incorporate longevity statistics based on the health of the individual.

It is noted above that the cost of heath care is the single largest financial burden faced in retirement. Over the last few decades health care costs have risen two to three times faster than inflation. Looking forward, the cost of medical care is projected to increase by as much as 15% annually. As a result, a 65 year old healthy female living to an actuarial calculated life expectancy of 89 will incur retirement healthcare expenses of $280,000 should she fall in the lowest income bracket to over $500,000 if she enters the highest income bracket.

In addition, the actual health care cost could even be higher if health care costs increase faster than projected. Moreover, if one becomes ill or one lives beyond the average life expectancy, one might need to be provided with nursing home care, where the average cost for a 65 year old female needing skilled nursing care in the State of Ohio can expect an average stay of approximately 3 years at a future cost of over $225,000 per year beginning at age 87.

With respect to commonly available insurance, it is noted that Medicare covers only half of health care expenses, and private insurance is often too costly and does not always address healthcare needs. These realities are causing forward looking consumers to assess the impact of health care expenses on their financial futures so that they can intelligently plan.

Thus, in the past there has not been a retirement planning tool that incorporates into individual plans personalized actuarial based longevity, as well as a calculation of health care expenses based on the health of the individual.

In order to overcome the shortcomings described above, the financial management tool described in the above noted patent application is provided which in addition to the usual financial profiling also considers an individual's health in order to project their heath care expenses during retirement. This tool also includes longevity calculations based on the personal health profile of each individual.

It is noted that financial advisors arbitrarily project lifespan and in many, if not the majority of cases, simply ignore health care expenses. As a result, there are health care expenses which are unaccounted for during the planning process that affects an individual's retirement.

Note this tool involves a method of calculating personal health care expenses and personalized longevity based on the particular medical history of the individual. This permits taking into account projected lifespan based on, amongst other things, health factors. Thus, if a person has high blood pressure or cancer; or is a smoker, the subject system projects a specific longevity as opposed to an average longevity. Moreover, these self-same considerations are utilized to project out annual health care costs during retirement. Additionally, the system accounts for accelerated healthcare expenses in the last two years of life which can create a substantial financial burden for extended family members.

With these two calculated inputs one can utilize the available comprehensive planning tools, and the subject system, to provide a comprehensive program tailored to the individual and not at the group level which is breaking new ground in the actuarial world.

In one embodiment, the system incorporates a questionnaire or profiling system that takes necessary items into account to calculate health care costs and longevity. This is then plugged into a database, in which the costs are broken down into different categories including Medicare Part A, Part B, Part D and Supplemental insurance premiums as well as other out of pocket expenses including co-pays eye, ear and dental expenses. The database for the individual is also broken down into specific disease states, such as heart disease, cancer, high blood pressure, cholesterol and the like. One embodiment of the system allows institutions to select from a 10 to 25 question health care questionnaire. This provides a report which calculates the projected amount of money that one will need to save in the present in order to cover future out of pocket health care expenses during retirement, all based on the individuals health history and expected lifespan. In one embodiment, the system takes the future value of retirement expenses as of the first year of retirement and based on an expected return on savings in retirement as well as the return on savings prior to retirement calculates how much the investor will be required to save today in order to cover future annual medical expenses in retirement. The system may output results in the net present value as well as future value.

Also inputted into the program is the current age of the individual, their proposed retirement age, their calculated life expectancy, the health care inflation rate, the expected rate of return prior to retirement, and the expected rate of return during retirement. The result of the financial tool calculation is the amount needed to be saved in order to cover future expenses, including health care costs.

The system is flexible in that one can choose a particular rate of return both prior to retirement and during retirement, and can then enter different retirement dates and to see the difference in the rates of return.

Obviously most individuals would not be as aggressive in their investments during retirement as they are in a pre-retirement period. This can also be reflected in the calculation made by the subject tool. As an example, if one is looking at a growth portfolio on a compounded basis, one may be looking at a 7% rate of return prior to retirement, but for instance a 4% return during retirement.

The important point is that the individual is given the opportunity to choose the rates of return and see what happens to the available funds. The calculation also enables one to project out what additional money needs to be saved per month if one cannot come up with an initial investment.

In summary, the above financial management tool permits an individual to know what are his or her costs going forward given a health-based prediction of how long the individual is expected to live.

This tool thus informs the individual of his options, calculates health care costs in his retirement planning, and gives him health-based longevity information that enables the individual to develop a comprehensive retirement plan.

The above the contrary not withstanding calculations have been based on survey date and a database that has a limited sample size.

SUMMARY OF INVENTION

It is the purpose of the subject invention to utilize actual claims made and the actual costs of resolving the claims as a basis for any healthcare related financial management tool. This invention relies on statistics from actual claims based on reports from the majority of health insurers. Moreover the database relies on current claims on the books of the health insurers and what the health insurers have to pay in resolving the claims. It is noted that the claims can be classified in terms of disease and particular patient condition, with the claims cross-correlated against the associated healthcare costs when the claim is paid.

Because actual claims and actual costs are placed in the databases where the database is used by a financial management tool one can provide a reliable healthcare cost estimate for use in retirement planning. The reason for the statistical reliability and prognostication value is the exceptionally large sample size and the granularity by which the claims can be analyzed. Moreover, this granularity can be correlated with associated actual costs to provide an unusual degree of confidence in the out put of the financial management tool that utilizes this database.

In summary, a financial management tool that includes calculated health care costs and health-based longevity to provide information to retirees to be able to calculate the amount of money that needs to be saved to cover retirement expenditures is provided with actual claims and actual related cost data from a database to increase the cost projection reliability of the tool.

BRIEF DESCRIPTION OF THE DRAWINGS

These and other features of the subject invention will be better understood in connection with the Detailed Description, in conjunction with the Drawings, of which.

DETAILED DESCRIPTION

Prior to describing the interaction of the actual claims, actual cost database with a financial healthcare centric financial tool are, the following describes such tool.

Figure 1:
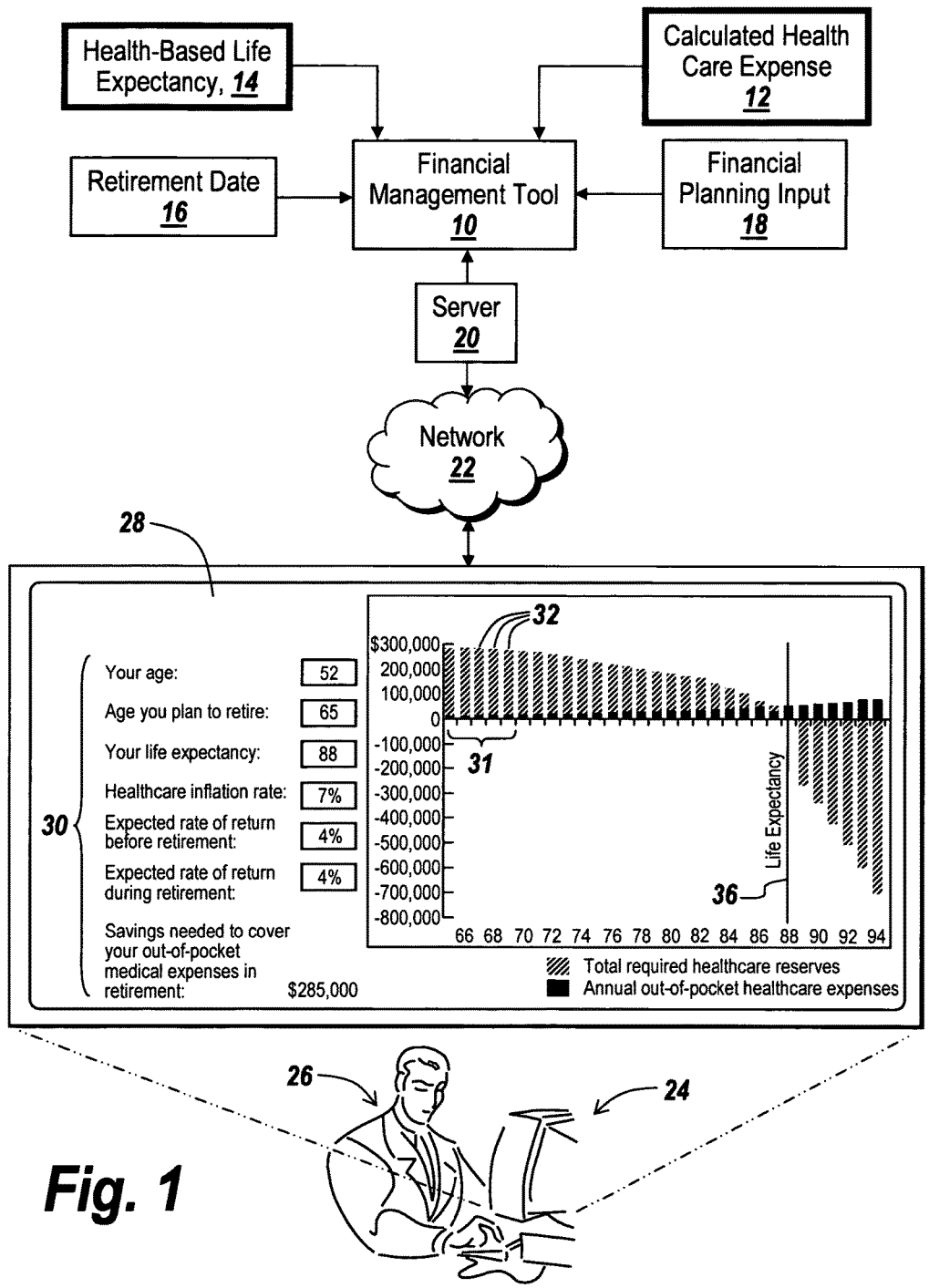
FIG. 1 is a diagrammatic illustration of the subject financial management tool utilizing health-based life expectancy and calculated health care expense to provide a display of cost of living versus available assets.

Referring now to FIG. 1, a financial management tool 10 is provided with both calculated health care expense 12 and health-based life expectancy 14. This takes into account health-based information to assist in financial management during retirement. Also, as an input to the financial management tool, is a selected retirement date 16 as well as a financial planning input 18 that includes expected state of residence, expected income in retirement, current savings and current and future rates of returns. Note that the financial management tool incorporates a processor for running algorithms that provides the calculations necessary for the subject invention including income and state of residency, as well as data storage.

The financial management tool 10 is coupled by a server 20 to a network 22 that may include the interne or some wireless communications vehicle, with the input to the financial management tool being from a terminal 24 operated by an individual 26. Here terminal 24 has a display 28 and enables input of relevant individual data in fields in the tool's data storage. The display of health-related information enables the individual to plan for retirement.

As can be seen on display 28, there are a number of fields 30 respectively relating to the age of the individual, the age that the individual plans to retire, the calculated life expectancy of the individual, the health care inflation rate, the expected rate of return before retirement, and the respected rate of return during retirement.

As a result of the operation of the tool a calculation is made to as the savings needed to cover the out-of-pocket medical expense portion of the expenses associated with retirement.

What is shown in the graph to the right of the display are the out-of-pocket medical expenses per year in retirement based on the information that has been provided in the dialog boxes to the left.

Assuming that an amount of savings needed to cover out-of-pocket medical expenses in retirement for a person age 52 who plans to retire at 65 and has a life expectancy of 88, what is displayed by columns 32 are the total required health care reserves. The shaded portions 34 show the annual out-of-pocket health care expenses. It is noted that the life expectancy 36 is derived based on not only average actuarial tables, but also actuarial tables taking into account the particular individual's health status.

As can be seen at age 65, in one example the amount of assets available is $285,000. This sum is decreased by the total required health care cost, with the out-of-pocket health care expenses increasing during the retirement years. What can be clearly seen from this chart is that the health care reserves are completely depleted at the calculated date of death.

Thus, the chart indicates that given all the health care information incorporated into the calculation, at the time of death one has completely depleted ones health care reserves. This is based upon initial savings, the health care inflation rate, and expected rate of return before retirement and expected rate of return during retirement.

This tool can be exercised by the individual by selecting values of the indicated variables, for example to compare the financial implications of retiring at one age as opposed to another.

One can also evaluate ones financial situation by varying the rates of return, both post-retirement and pre-retirement.

Figure 2:
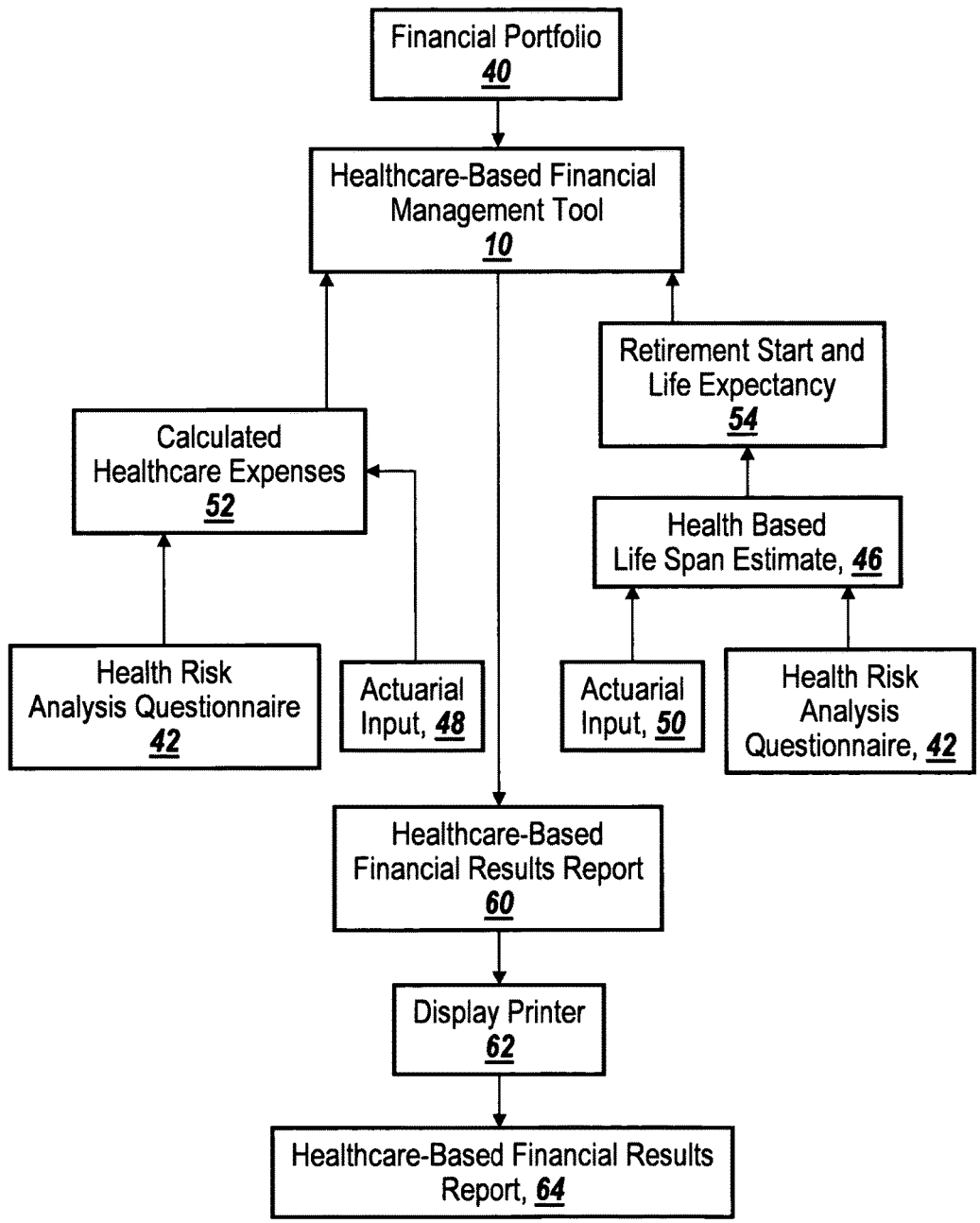
FIG. 2 is a block diagram of the system of FIG. 1, in which the results of a health risk analysis questionnaire are provided to project health care costs and to provide health-based lifespan estimates.

Referring to FIG. 2, financial management tool 10 has its financial planning input from a financial portfolio 40 in which various investment portfolio scenarios can be entered into tool 10.

Most important, with respect to this financial planning tool, are the health care based initiatives engendered by the completion of the health risk analysis questionnaire 42, which is used both to provide information about and to project health care costs as illustrated at 44, and to deliver a health-based life plan estimate 46. There is an actuarial input 48 to enable the projected health care costs to be calculated at 52, as well as an actuarial input 50 to be able to provide for a health-based life span estimate.

The projected health care costs are the health care expenses calculated at 52, whereas the health-based life span estimate 46 is utilized to populate a module 54 that defines the retirement start date and the life expectancy of the individual.

As shown, a health care based financial results report 60 is supplied to a display or printer 62 from which health care based financial reports can be viewed as illustrated at 64.

Figure 3:
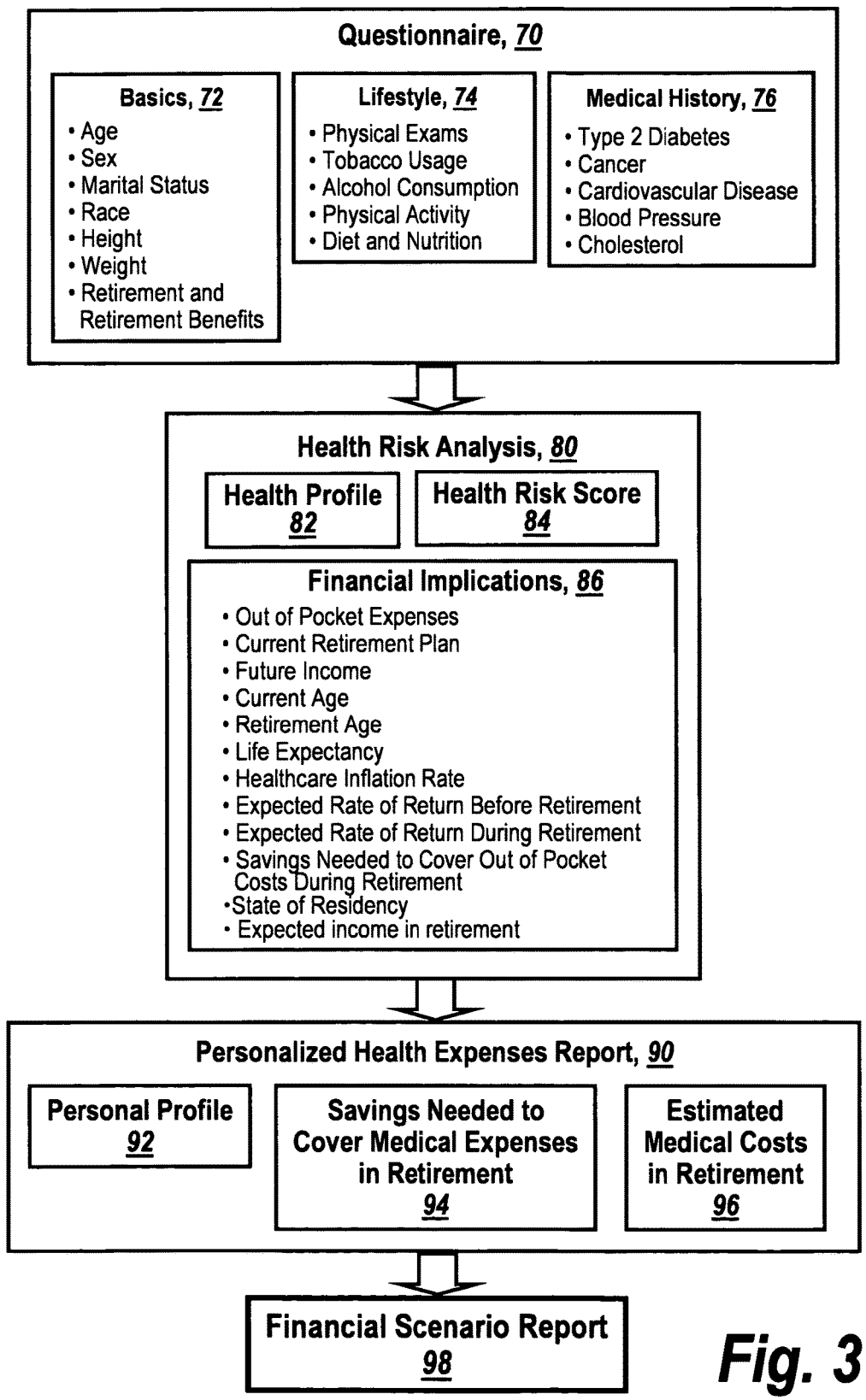
FIG. 3 is a diagrammatic illustration of the health care questionnaire utilized in the subject invention, which incorporates basic information about the individual, lifestyle and medical history to provide a health risk analysis that results in a personalized health expense financial management tool that calculates the savings or income needed to cover out-of-pocket costs during retirement.

Key to the financial management tool is the health care questionnaire shown in FIG. 3, designated by reference character 70. Here the health care questionnaire 72 incorporates basic information such as age, sex, marital status, race, height, weight and answers to types of retirement plans and retirement benefits. The questionnaire also includes a lifestyles portion 74 that incorporates the result of physical exams, tobacco usage, alcohol consumption, physical activity, and diet and nutrition.

The questionnaire also includes a medical history section 76 that includes medical indicators, such as type 2 diabetes, cancer, cardiovascular disease, blood pressure, and cholesterol numbers.

The result of the questionnaire is applied to a health care risk analysis module 80 that includes a health profile 82 generated from questionnaire 70, as well as a health risk score 84.

The health risk analysis creates the financial implications 86 so as to provide entry into a financial plan for instance out-of-pocket health care expenses.

Module 80 having calculated the various financial implications outputs a personalized health expenses report 90, which includes a personal profile 92, the savings needed to cover medical expenses in retirement 94, and the estimated medical costs in retirement 96. These implications are contained in a final financial scenario report 98.

It is thus important for the individual planning for retirement to be able to know what amount to set aside for retirement by taking into account not only the usual financial analysis tool outputs, but also modification of these outputs that account the health of the individual.

Figure 4:
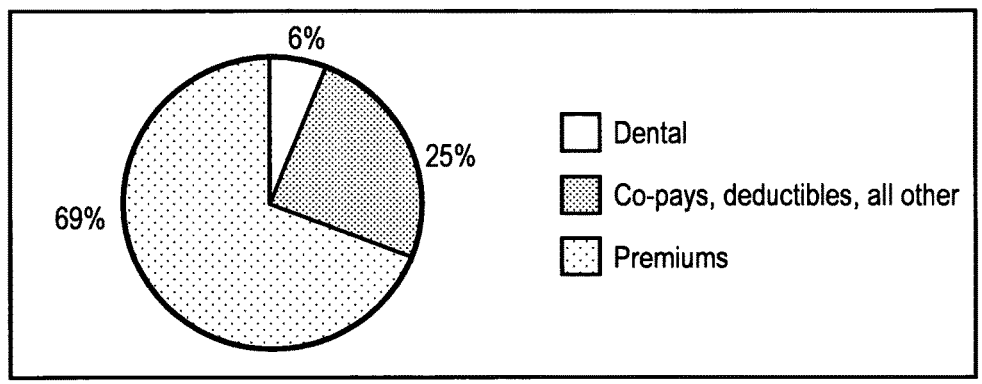
FIG. 4 is a pie chart showing projected out-of-pocket health care expenses broken up into dental, co-pays and premiums.

Referring to FIG. 4 as can be seen from the pie chart, typical projected out-of-pocket health care expenses are 69% due to premiums, 25% due to co-pays, deductibles and all other expenses, and about 6% due to dental costs.

Figure 5:
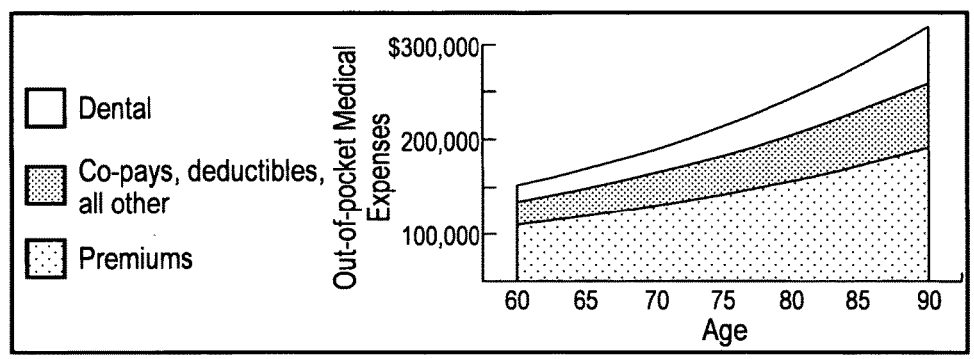
FIG. 5 is a graph showing expense growth over the course of retirement years for dental, co-pays and premiums.

Referring to FIG. 5, these projected health care expenses grow over the course of retirement years. For example, the combined dental, co-pay and premium cost at for instance age 60 of $150,000 balloons to over $300,000 if the individual lives to the age of 90.

Figure 6:
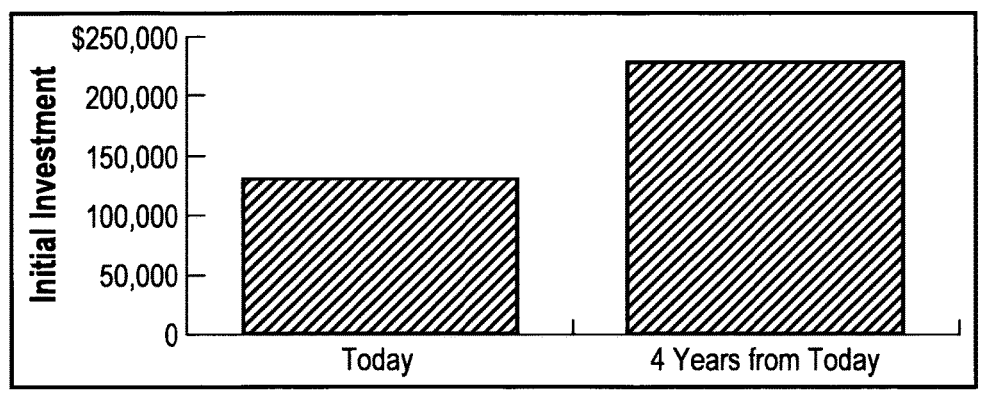
FIG. 6 is a graph showing the cost of waiting to enter into a retirement program based on current assets available versus costs in four years.

Another useful output of the financial management tool is calculating the cost effect of waiting for retirement. As can be seen by the graph in FIG. 6, assuming that one has a current health care cost of $140,000, it can be seen through the use of the subject tool that waiting for 4 years to begin retirement would result in an overall cost increase of approximately $250,000, showing that delay in retirement planning is indeed costly.

Figure 7:
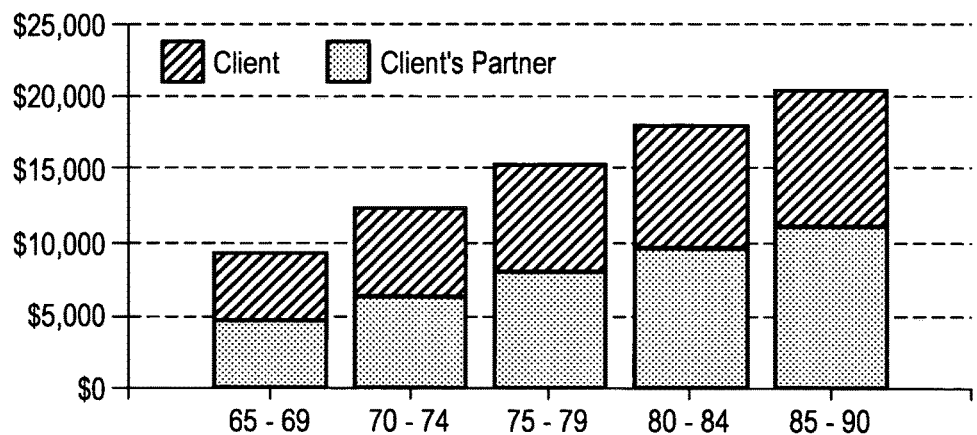
FIG. 7 is a bar chart showing estimated medical costs in retirement for both the client and the client's partner over five year retirement periods.

Referring to FIG. 7, one of the interesting outputs of the financial management tool is the ability to provide a visual output of the estimated medical costs in retirement over five year increments and to show the increase in estimated medical costs for either an individual or their partner. Here the estimated medical costs in retirement can be computed on a five year interval based on a combined input from the client and the client's partner. Note, if the client dies at 90 years of age, the client's partner's estimated costs are shown for the following four years.

Figure 8:
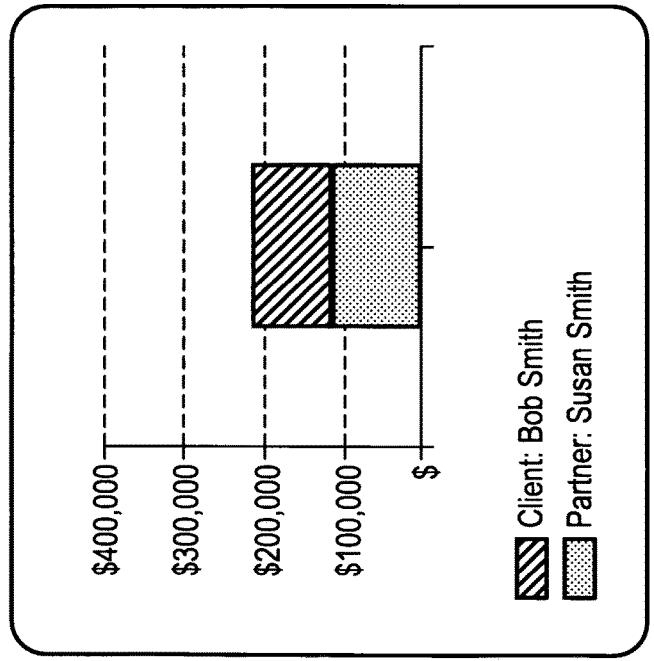
FIG. 8 is a diagrammatic illustration of the estimated medical costs in retirement, which compares savings needed to cover medical expenses in retirement versus actual medical expenses in retirement, showing the advantage of early investing.
Figure 9A:
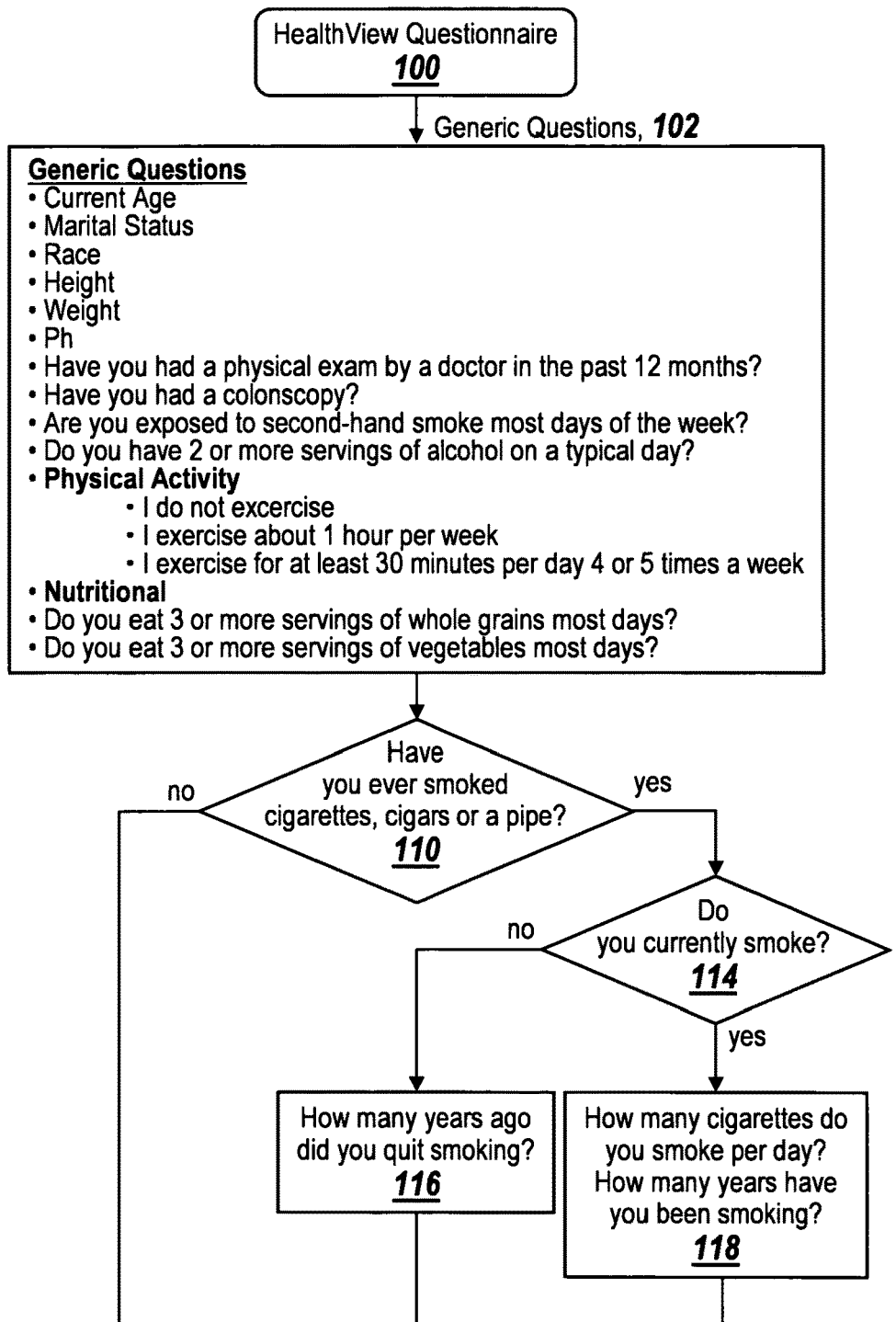
FIGS. 9A-9E are flow charts showing the operation of the subject system.
Figure 9B:
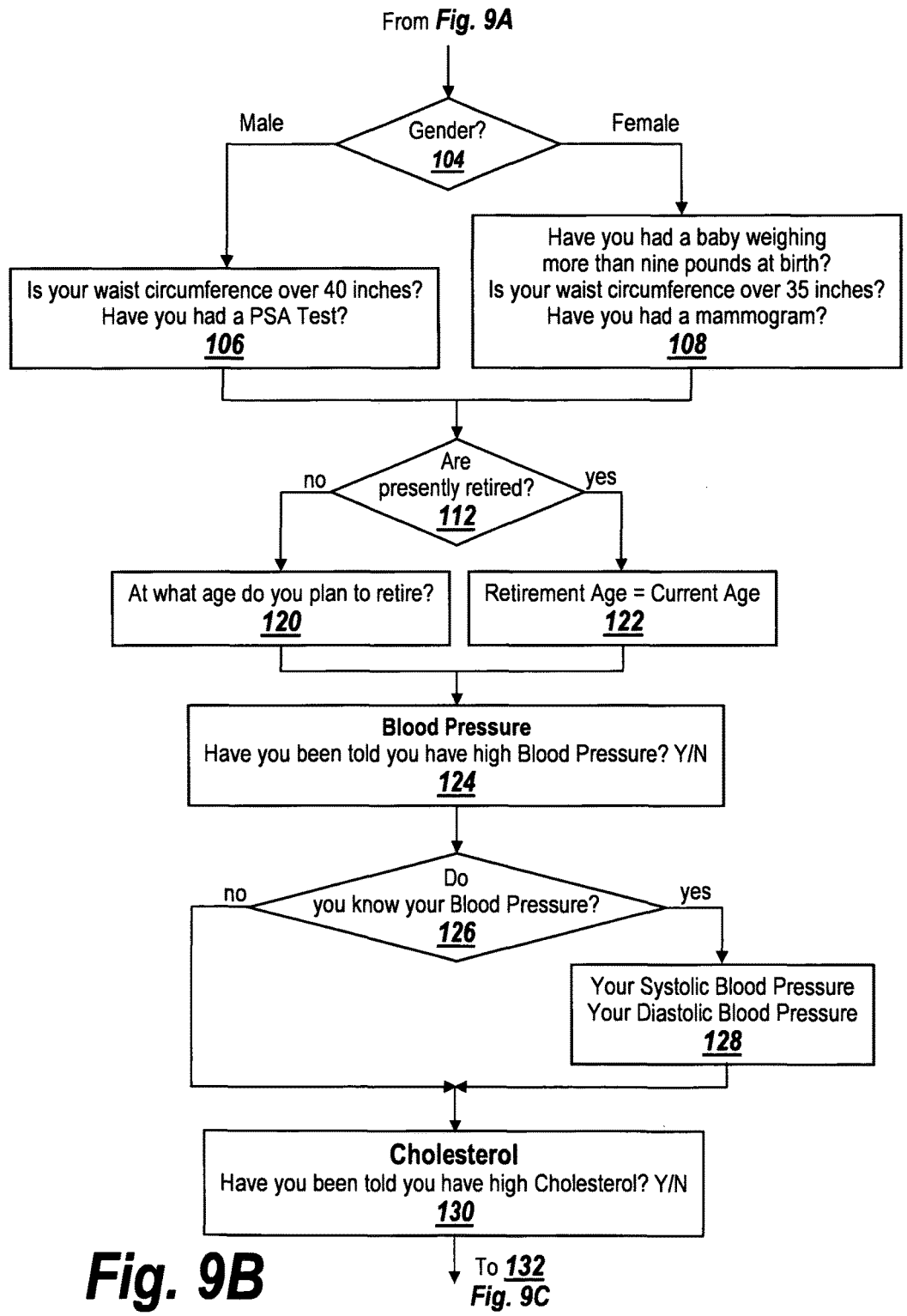
Figure 9C:
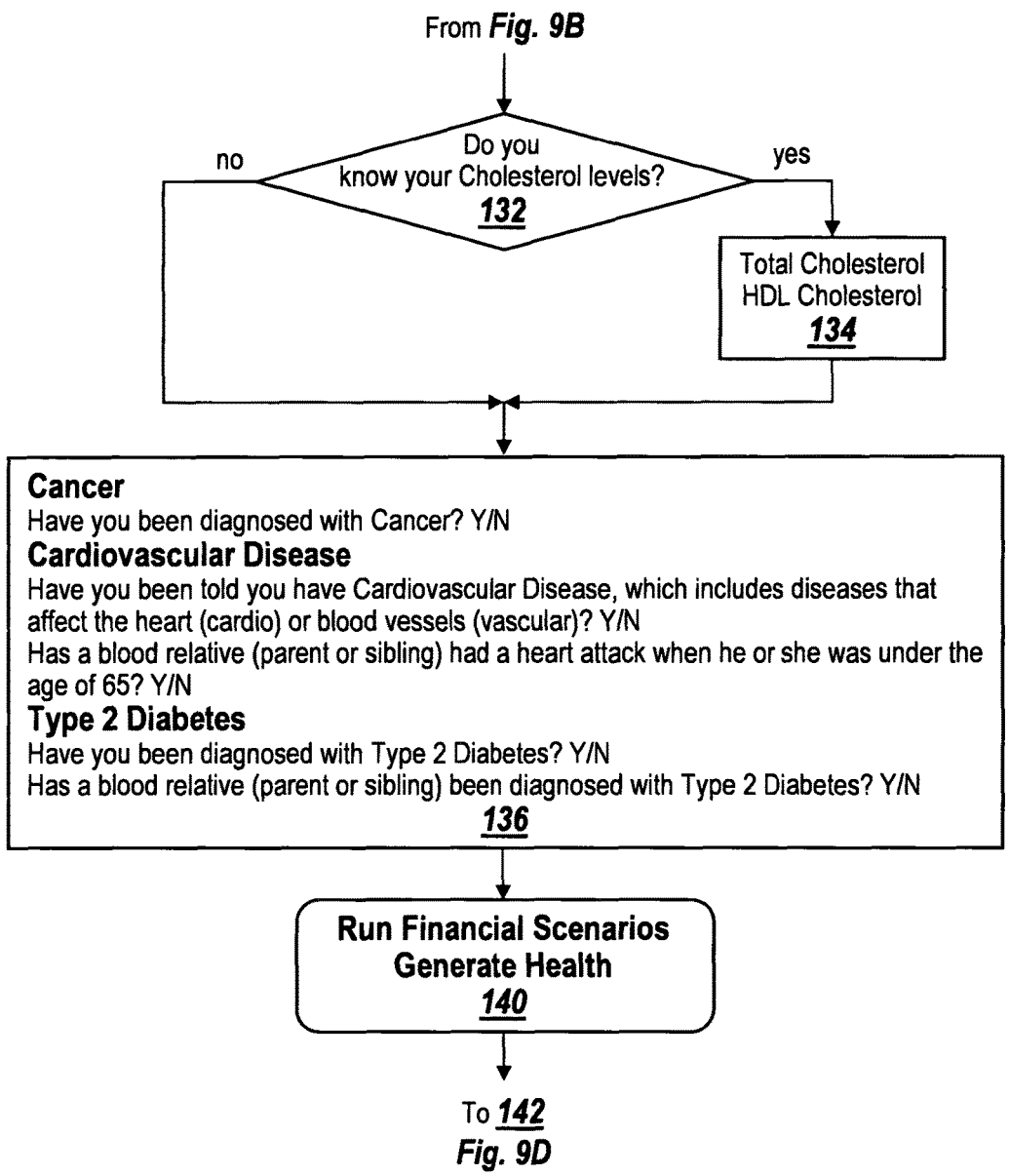
Figure 9D:
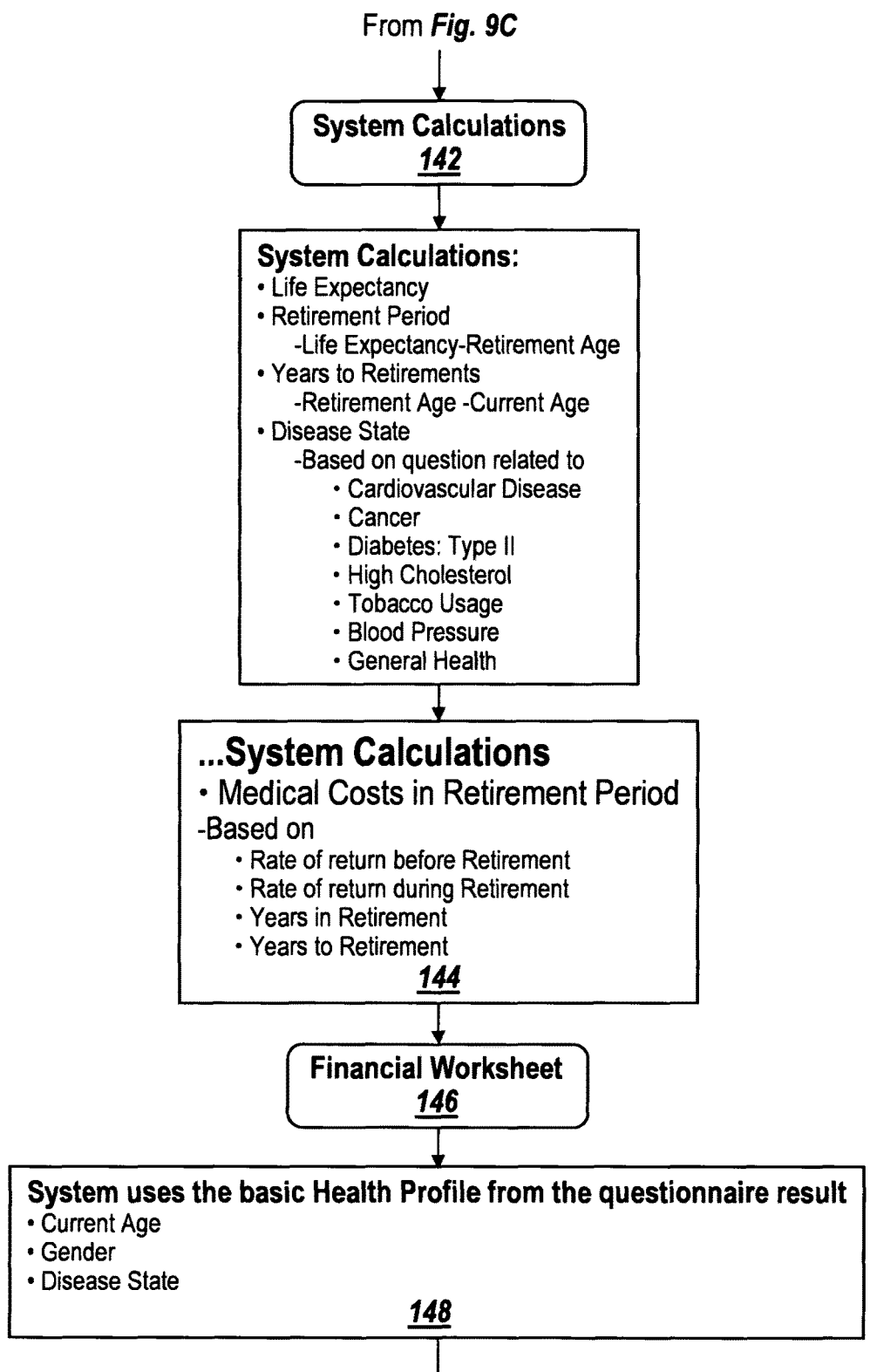
Figure 9E:
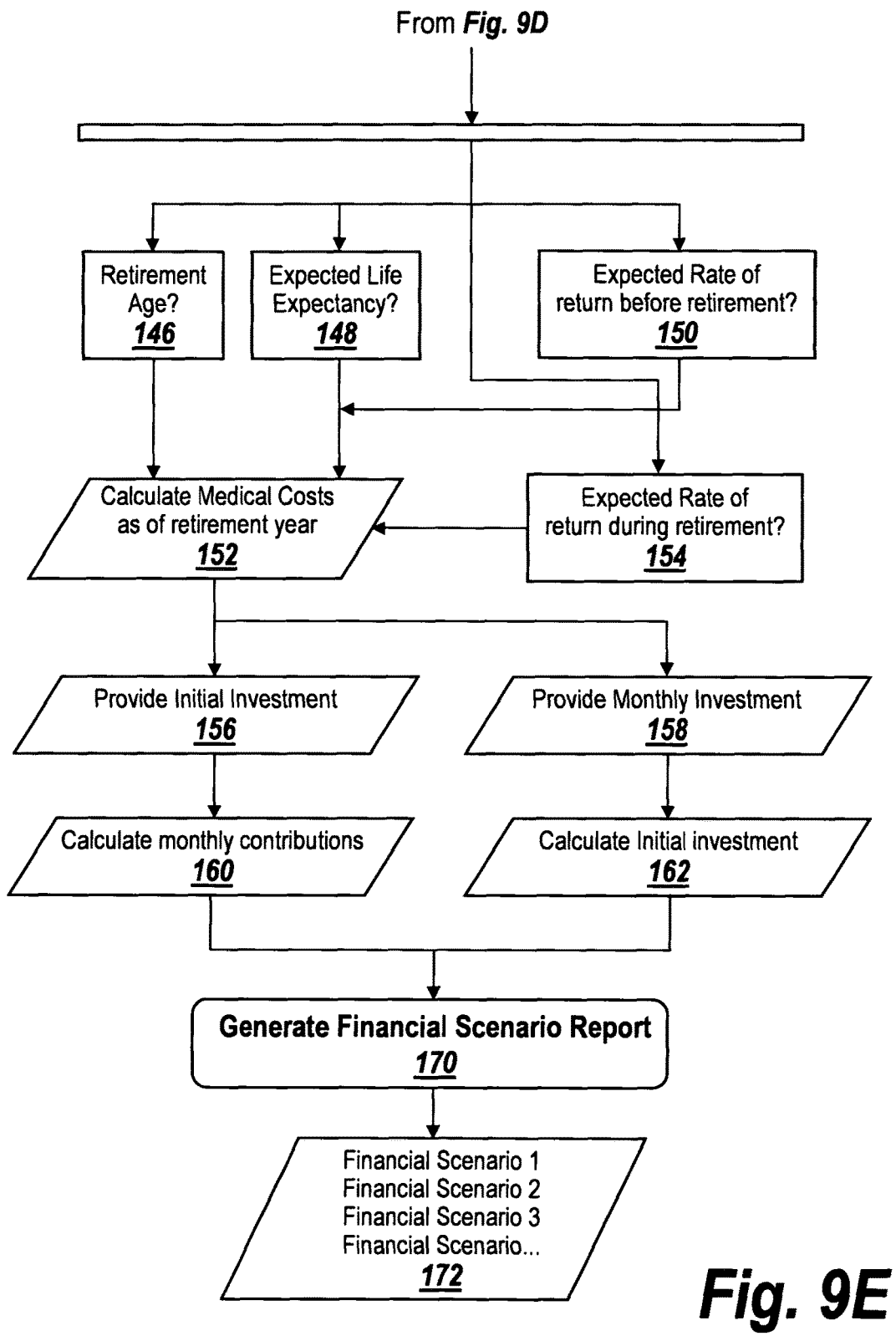

Referring now to FIG. 8, shown are two bar graphs that indicate the savings needed to cover medical expenses in retirement, for instance $216, 261 for an individual versus the medical expenses in retirement, which are calculated to total $397, 587.

This indicates that early investing is needed to offset the total medical expenses in retirement, which typically exceed the savings necessary to cover these expenses.

In summary, what is provided by the financial management tool is an individualized report that calculates the necessary savings needed to cover medical expenses during one's retirement years. Since these medical expenses are the most significant expense during retirement, providing an individual with a calculation of the savings they can determine when to retire and what assets or savings would be required to cover their health care expenses.

What follows are examples of how an individual can benefit from the use of the subject financial management tool.

Example I

As mentioned above, the primary use of the financial management tool is to determine how much money one will need to have saved at the point of retirement. Based on the retirement date and the expected return on savings and retirement, the financial management tool calculates how much savings must be accumulated in order to cover annual medical expenses.

For instance, a particular individual may need $120,000 in savings to cover $120,000 in health care expense. Note that the health care expense is growing at about 5% annually. Assuming $120,000 in savings is required at the point of retirement, the system can calculate from today's date until the retirement date what one would need to save. For instance, one would need $38,000 in the present in order to have $120,000 at the point of retirement to cover the medical expenses.

Since medical expenses are the largest expense during retirement, it is not an expense that can be diminished by living in a smaller house or buying a less expensive car. One does not have these options with health care. Thus, the numbers that are going to have to be addressed are the actual projections based on the individual's health and status.

Example II

Another feature as mentioned before is that if a person needs $38,000 in savings today in order to have access to $120,000 at retirement, the financial management tool will inform the individual that if they have only $20,000 today, the subject tool will suggest they add an additional $32 per month to reach their goal.

Example III

As noted above, one can choose rates of return and can run "what if" scenarios. For instance, the system can reflect the various financial implications of retiring at 65 years of age or at 67 years of age. The tool can be adjusted to various retirement dates and also on different rates of return during retirement.

If, for instance, one is involved in a growth portfolio on a compounded basis, the individual may be looking at 7% growth. However, during retirement assuming the portfolio is more conservative and goes to purchasing of treasuries, perhaps a 4% rate of return is a more reasonable rate. Thus, the individual gets to choose their potential rates of return and sees what happens to the numbers.

Example IV

As mentioned before, retirees can use the financial management tool to calculate the cost going forward into retirement. One of the critical elements is determining an individual's life span. This becomes problematic with age. A healthy 40 year old has a very specific life span whereas a healthy 68 year old life span will be significantly longer than a healthy 40 year old, the extent to which is difficult to judge. Thus, a person that is 68 would need to know their likelihood of living past 80 or 90 and what their health care expenses will look like.

Example V

Retirees generally operate on a budget and must know what the impact their medical cost will have on their budget. Once this calculation is done the question then becomes how long will their money last.

For instance, if the individual is spending between $3,000 and $4,000 a year on vacations that they were hoping to do on an annual basis until they are 75, they may be persuaded by the subject calculations to alter their spending habits. In order to inform the individual, one first has to calculate their health care expenses. Then one has to provide a budget in today's dollars.

For instance if the budget is $30,000 a year for medical expenses, by the end of a 15 year period in which a 3% inflation rate is constant, medical expenses may be over $60,000 a year. It is important for individuals to know these numbers when establishing their budget and the subject tool in determining these adjusted costs. The next budget step is income sources. Assuming that one has a half a million dollars in savings, is going to generate $24,000 out of social security, has a small pension, and could potentially sell his or her house, the subject tool can calculate a distribution analysis on a year by year basis to show how ones assets are dwindling and when they will run out. If one knows that one is going to be living in retirement for 30 years one could be out of money in 20 years. Thus creating a budget that takes into account the health care costs is an exceedingly useful function for the subject tool.

Example VI

As mentioned above, firms with over 100,000 employees are self-insured. The question of raises for employees presents certain problems. For instance, one needs to know whether to give an employee a 5% raise and how much the raise is really worth. With the financial management tool the company can quickly plug in a 7% increase in health costs so that in this scenario the employee is being given a 12% raise.

Example VII

The financial management tool provides realistic numbers based on a persons health history and other actuarial characteristics and provides disease management and wellness advice. As mentioned above, if an employee can better manage their health care then cost savings can be significantly augmented. For instance, if an individual knows his age and health status, the financial management tool can output the life span of the individual. It is then possible to calculate the annual cost of health care because the company knows what portion the individual pays for and what portion the company covers. For example, if the individual does not follow a doctor's prescribed plan, instead of living to 78, the life span could be 67. There are associated annual costs for health care for the individual between the present time and age 67 which, for instance, may be different than the annual cost between the present time and 78. With successful coaching information can be provided to the employee as an incentive to take the right action.

For instance, if the individual has type 2 diabetes and does not take care of his condition he may die by the time he is 67 years old. If he takes care of himself properly he may live to 78. Calculations from the calculator may indicate that he will be spending $800 a year if he takes care of himself, whereas he may be spending $1,400 if he does not take care of his condition.

What is now presented are a series of flow charts to indicate how the subject calculator operates.

Referring now to FIGS. 9A-9E, the process used by the financial management tool starts with a questionnaire 100 which poses generic questions 102, namely questions such as current age, marital status, race, height, weight, ph, whether you have had physical exam by a doctor in the past 12 months, whether you have had a colonoscopy, how often you are exposed to second-hand smoke, do you have two or more servings of alcohol in a typical day, your level of physical activity, and your eating habits The output of the generic questions is applied to a decision block 104 which then takes the individuals gender into account. If male, then the question is asked as illustrated at 106 "is your waist circumference over 40 inches", or "have you had a PSA test". If female, at 108 the question is asked "have you had a baby weighing more than 9 pounds at birth", "is your waist circumference over 35 inches" and "have you had a mammogram".

The results are passed to a decision block 110 which poses the question "have you ever smoked cigars, cigarettes or a pipe." If no, then the answer is passed to decision block 112. If yes then as shown at decision block 114 the question is posed "do you currently smoke". If no, the question is asked as illustrated at 116 "how many years ago did you quit smoking". If the answer is yes, the question posed at 118 is "how many cigarettes do you smoke per day and how many years have you been smoking."

The results of the outputs of blocks 116 and 118 are also applied to decision block 112 which asks the question "are you presently retired." If the answer is no, then as illustrated at 120 a query is asked as to "what age do you plan to retire." If yes, then the retirement age is set to ones current age as illustrated at 122.

The results are passed to block 124, which poses the question "have you been told that you have high blood pressure yes or no." If yes, then as illustrated by block 126 the question is posed "do you know your blood pressure." If yes, the question is posed at 128 to provide your systolic blood pressure and your diastolic blood pressure.

The outputs of these blocks are passed to a block 130 to ascertain if you have been told that you have high cholesterol, yes or no. The result is passed to decision block 132 which asks the question "do you know your cholesterol levels." If yes, the question asked at 134 as to what your total cholesterol is and your HDL cholesterol level.

The outputs of these blocks are both sent block 136 which asks the questions relating to disease, namely "have you been diagnosed with cancer yes or no", "do you have cardiovascular disease, yes or no", "have you been told that you have cardiovascular disease which includes diseases that affect the heart (cardio) or blood vessels (vascular) yes or no." Also a question is posed "has a blood relative either parent or sibling had a heart attack when he or she was under the age of 65." Again an answer yes or no is recorded. Finally the question is asked "have you been diagnosed with type 2 diabetes yes or no", or "do you have a blood relative, parent or sibling that has been diagnosed with type 2 diabetes yes or no." The results are passed to a module 140 that runs financial scenarios at 140 which employs system calculations 142. These calculations include for instance life expectancy, retirement period in terms of life expectancy minus retirement age, years to retirement, i.e. retirement age minus current age, disease state based on questions relating to cardiovascular disease, cancer, type 2 diabetes, high cholesterol, tobacco usage, blood pressure and general health. The system calculations as illustrated at 144 result in a calculation of medical costs in the retirement period based on the rate of return before retirement, the rate of return during retirement, years to retirement, and years in retirement.

The output of the system calculations 144 is reflected in a financial worksheet 146 in which the system uses the basic health profile from the questionnaire to indicate current age, gender and disease state as illustrated at 146.

From this financial worksheet one ascertains retirement age as illustrated at 146, expected life expectancy 148 and the expected rate of return before retirement at 150, the outputs of which are referred to a calculator that calculates medical costs as illustrated at 152, which in turn is reflected in the expected rate of return during retirement as illustrated at 154. The calculated medical costs are then inputted to a module 156 that, calculates monthly investment 158, monthly contributions 160 and the initial investment 162. Finally at 170 a financial scenario report is output which provides a number of different financial scenarios based on a number of different variables, all of which are viewed at 172.

Calculating Healthcare Expense

After the HealthView questionnaire is completed the system determines health status and calculates life expectancy based on Current Age, Gender and Disease state. The information is saved in a database and used in calculating detailed healthcare costs.

The financial management tool utilizes stored procedures to calculate the medical costs that are required in retirement from actuary tables.

The stored procedure Input parameters are:
Client
   Current Age
   Gender
   Disease State
   Expected Life Expectancy
   Retirement Age
Spouse (if spouse information collected)
   Current Age
   Gender
   Disease State
   Expected Life Expectancy
   Retirement Age
Rate of Return before Retirement
Rate of Return during Retirement
Flag to determine if calculation should be at Net Present Value or at Pesent Value as of Retirement Year The stored procedure returns a data set that is comprised of multiple data tables.

These data tables are used to populate graphs, charts and grids on the reports and forms.

Processing Steps

The stored procedure performs the following steps:
Get information from Actuary tables to a local data table based on input parameters from retirement age to 100 for client and spouse; the data table being populated with:
   ItemRetId
   ClientID—Client or spouse
   DiseaseState
   Gender—M/F
   Current Age
   Calculated Year
   LifeExpectancy
   AttainedAge
   Total out-of-pocket expenses
   Hearing
   Vision
   Premuims
   Dental
   TotalCost
   Adjusted out-of-pocket expenses
   Adjusted Premuims
   Adjusted Dental
   Adjusted Total Cost
   Healthcare Cost in Retirement
   HealthcareCost During Retirement
Set ItemRetId as a difference between attained age and retirement age Calculate adjusted costs to Present Value as of Retirement year for client and spouse using:
HealthcareCostinRetirement
AdjustedPremuims
AdjustedDental
AdjustedTotalCost Calculate total costs as of Retirement year for client and spouse based on the retirement period (retirement age to expected Life expectancy)

Calculate time to horizon (Retirement age—current age) and calculate investment Required at Net Present Value Determine the joint retirement period Lowest retirement age to largest life expectancy and determine the three cut-off groups based on the earliest retirement of the two and oldest life expectancy using data related to:
Client
Spouse and Client
Spouse
Or:
Spouse
Spouse and Client
Client Calculate Total Costs for Client and Spouse in Retirement Periods Create Output data table that includes annual costs for premiums, out-of-pocket expenses, dental, hearing, vision and total costs for client, spouse and Total for both. Create Output data table that includes annual costs, and average costs at a selected interval during retirement period (default every 5 years) for client, spouse and for both The table includes premiums, dental and out-of-pocket expenses, hearing and vision Create Output data table for client and spouse that displays
Retirement category
  Retirement
  at retirement year
  during retirement
Initial investment
Period—number of years
Slope (%)

The information from the tables provides estimated projected costs closest to actuary tables for graphs and planning tools.

Create an output table with all data collected and processed from the current age to 100 to allow use of the raw data in calculating what if scenario, update grids, charts and graph.

Create a summary output table of cost required for client and spouse

The source code for the financial management tool is attached as an appendix hereto.

Actual Claims, Actual Cost Database

As stated hereinbefore it has been found that the accuracy of the financial predictions of the subject financial management tool can be immeasurably improved utilizing actual claims data and actual cost data for these claims.

Figure 10:
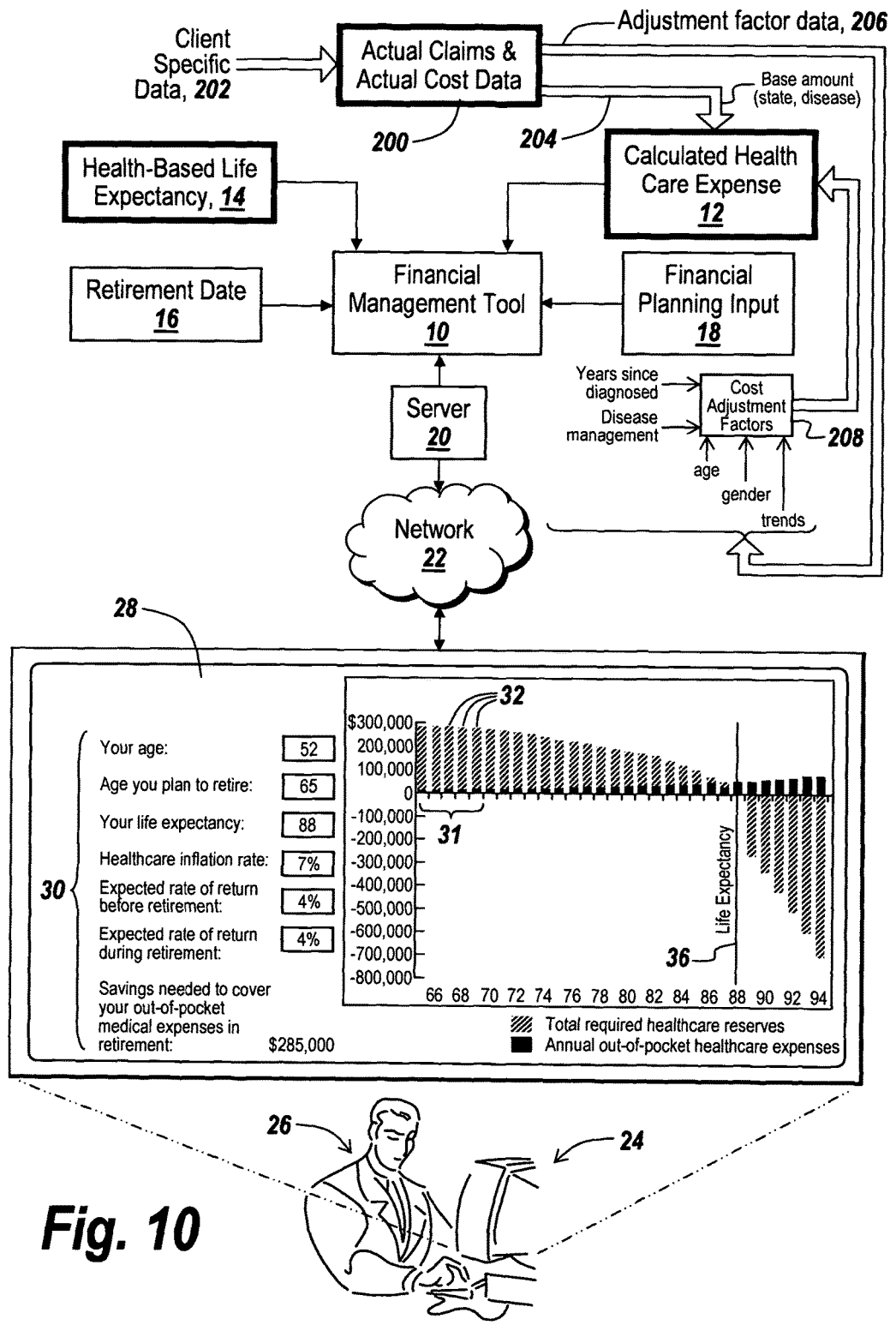
FIG. 10 is a diagrammatic representation of the use of actual claims and actual associated costs in providing precise actuarial data to the covered healthcare expense module of FIG. 1.

Referring now to FIG. 10, the financial tool of FIG. 1 is replicated, with items carrying like reference characters.

Added as an overlay to the system of FIG. 1, as shown in FIG. 10 an actual claims and actual costs database 200 is utilized to develop a base amount for a given illness or disease based on the state of retirement for the particular individual as input in terms of specific client data 202. This base amount here indicated, by arrow 204, is coupled to the calculated healthcare expense module 12, along with adjustment factor data 206 from database 200. This adjusted factored data is applied to a cost adjustment factor module 208 which in one embodiment adjusts the base amount output from database 200 for instance by years since the disease was diagnosed, the disease management regime, the age, and the gender of the client as well as certain trends. All of these factors are combined as an adjustment factor to the base amount from database 200.

Figure 11:
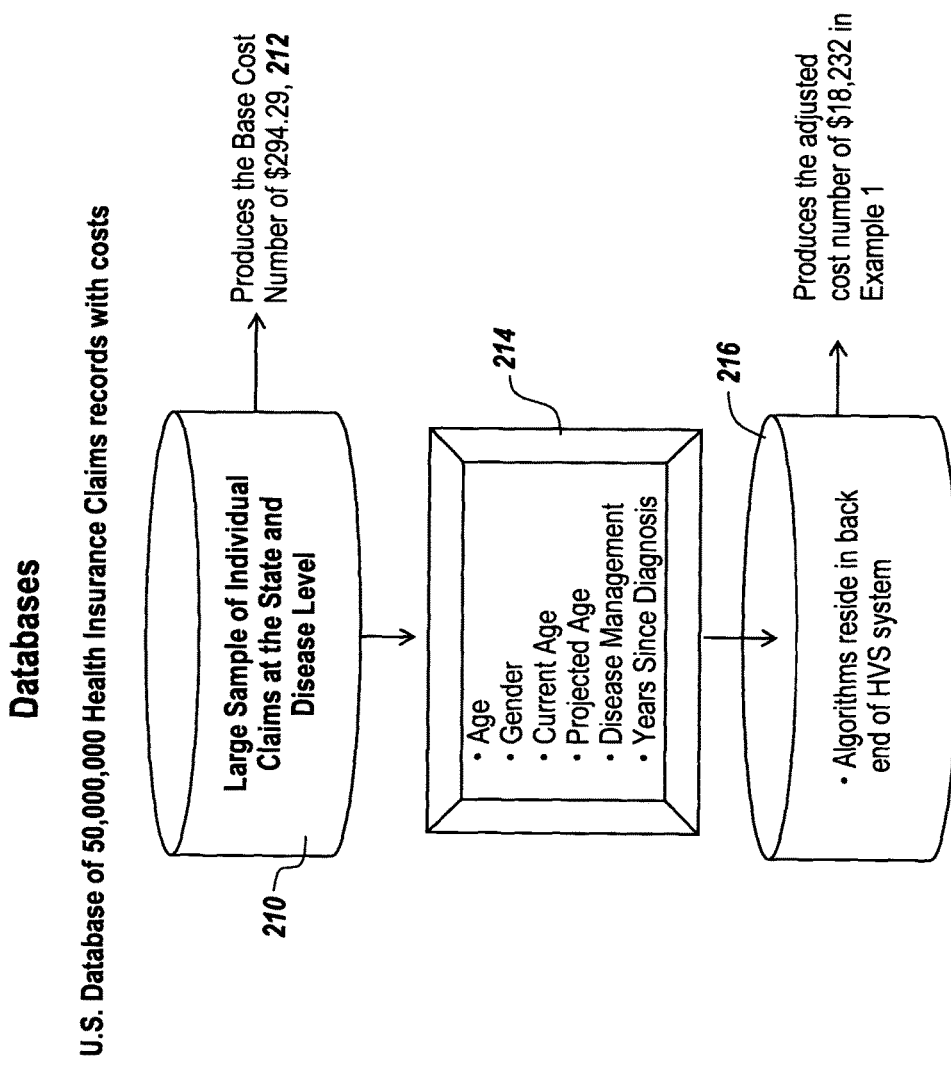
FIG. 11 is a flow chart of the actual claims and actual cost database of FIG. 10 showing the generation of base healthcare cost number and the cost adjustment due to an individual's profile; and, FIG. 12 is a healthcare centric chart for deriving an age appropriate hospital cost based on the actual claims and actual cost database of FIG. 10.

Referring now to FIG. 11, the databases utilized in the subject invention include for instance a U.S. database of over 50 million health insurance claims records and costs. This large sample, illustrated at 210, is a large sample of individual claims arranged according to state and disease level which for instance produces a base cost 212, in one embodiment for instance $294.29. Database no is also queried as to the individual profile entered into the front end of the system which items determine which factors need to be adjusted from the base cost.

In one embodiment as illustrated 214 these items involve an adjustment factor for age, gender, current age, projected age, disease management regime, and years since diagnosis. These items are then provided as inputs to algorithms that reside in the subject system, namely algorithms 216, which for instance produce in one embodiment an adjusted cost for hospital care in the amount of $18,232.00 in an example to be described in FIG. 12. Note that items 214 are stored in cost adjustment module 208 of FIG. 10 and include for instance how the disease is managed, costs in the last two years of life, long term costs, annual updates to projections based on cost trends, regular updates from the Affordable Care Act and other factors. It is these factors which drive algorithms 216 such that given a base cost of $294.29 the adjusted cost number in one example for instance of a poorly managed health regime is $18,232.00.

How these adjustments are applied is shown in the table of FIG. 12. Here the information is for a 45 year old male in Alabama with poorly managed diabetes. The information in the table of FIG. 12 shows how the base cost estimate of $294.29 is adjusted for the profile of the individual for a 21 year projection to 2033, age, gender, disease management and years since diagnosis to produce a total out-of-pocket hospital cost of $18,232.43 in 2033.

It will be seen that the $18,232.43 cost relates to the hospital costs for an individual age 65 in the year 2033 which is derived as follows. The base amount for the hypothetical 45 year old male is $294.29 based on a diabetes type II managed poorly scenario. This cost is derived from database 200 and utilizes actual claims and actual cost data.

It is noted that in this case that the disease was diagnosed less than a year ago. This number is trended forward 21 years at a rate of 7% to yield a cost of $1,218.52. Thereafter one applies and age/gender factor of 971.610% to yield a hospital cost of $11,839.24. Following this is applied a disease management factor for the poorly managed scenario noted of 154.000% which yields a hospital cost of $18,232.43. It is noted that this is one of the costs associated with healthcare in a person's retirement based on a 21 year projection.

From what has been presented the creation of adjustment factors for the base cost involves a full set of base cost data tables and adjustment factors created for each of the cost items shown across the top of the table in Example 1, namely medical premium individual, Rx premium individual, medical premium employee base, Rx premium employee base, dental premium, hospital out-of-pocked (OOP) costs, doctor and tests OOP costs, Rx OOP costs, dental OOP costs, hearing OOP costs, vision OOP costs and others using the actual claims data records and costs available in database 200.

As to the base cost data the table shown below is only for hospital OOP costs. The base data for the hospital OOP costs are taken directly from the claims database for each state and chronic disease condition. These costs are shown below.

| | Costs for 2013 | | |
|---|---|---|---|
| State | High Blood Pressure | High Cholesterol | Diabetes |
| AL | $200.44 | $144.03 | $294.29 |
| AK | $340.25 | $244.60 | $499.68 |
| AZ | $232.80 | $167.44 | $342.04 |
| AR | $167.16 | $120.26 | $245.59 |

Note in one embodiment rather than creating a similar table for every possible characteristic or combination of characteristics in a patient's profile such as current age, gender, life expectancy and income and for every possible year that the individual ages into through retirement, the database creates a set of adjustment factors. This constitutes a thinner set of adjustment factor formulas which allows the subject system to contain significant less raw data and thus decrease the time in which a cost estimate can be produced.

Once an individual's profile information has been input, the adjustment factors are applied to the base cost data to appropriately reflect correct costs for that particular individual.

It is noted that the adjustment factors are also derived directly from the claims database and are stored as a separate file. Every time the system is updated with any particular type of legislative, cost trend or other changes, both the database table files and the adjustment factor files are imported into the subject system.

The adjustment factor file is created from the original claims data file as follows.

First a statistical software program such as SAS or SPSS is run on the claims database. This program compares the cost data in each of the columns of actual cost data as illustrated below and creates an adjustment factor. This can be seen below.

The data in these columns to predict future costs come from predictive or prognostication algorithms that take the actual historical base cost data and compare it to for instance the prior 10 years history of cost increases to accurately predict trends.

From the above, the following are the cost adjustment factors:

| | | Adjustment Factors | | | |
|---|---|---|---|---|---|
| State | Diabetes Patient Costs in 2013 (Base Costs) | Cost Adjustment Factor For 5 Year Cost Increase by 2018 | Cost Adjustment Factor for Male 65 Years Old in 2018 | Well-Managed Disease Cost Adjustment | Poorly Managed Disease |
| AL | $294.29 | 414.06% | 971.61% | 75.0% | 154.0% |
| AK | $499.68 | 414.06% | 971.61% | 75.0% | 154.0% |
| AZ | $342.04 | 414.06% | 971.61% | 75.0% | 154.0% |
| AR | $245.59 | 414.06% | 971.61% | 75.0% | 154.0% |

As can be seen the adjustment factors are compiled utilizing actual costs and projected increases in cost as the year's progress.

Next using a statistical methodology known as analysis of variance or ANOVA, the adjustment factors tested for statistical accuracy and reliability. This test typically requires a very large number of claims in each of the above columns for instance a minimum of over 2,000 claims, in order to be statistically reliable. Only the adjustment factors which were statistically reliable will be saved in cost adjustment factor module 208 of FIG. 10.

What will be seen is that actual claims data and actual costs of resolving the actual claims are used both for the base number for a particular state and disease, as well as in formulating the adjustment factors which are used to adjust the base cost. As a result a financial management tool which utilizes both the actual claims and actual costs involved resolving the claims results in a highly sophisticated extremely accurate predictor of healthcare costs in the retirement of the client.

While the present invention has been described in connection with the preferred embodiments of the various figures, it is to be understood that other similar embodiments may be used or modifications or additions may be made to the described embodiment for performing the same function of the present invention without deviating therefrom. Therefore, the present invention should not be limited to any single embodiment, but rather construed in breadth and scope in accordance with the recitation of the appended claims.

| | Actual Hospital OOP Costs From Claims Data for Each Defined Group of Claimants | | | | |
|---|---|---|---|---|---|
| State | Diabetes Patient Costs in 2013 (Base Costs) | Diabetes Patient Costs Increase Over Base in 5 Years (to 2018) | Diabetes Patient Costs for Male, 65 yrs. old in 2018 | Well-Managed Diabetes Patient Costs for Males, 65 yrs. old in 2018 | Poorly-Managed Diabetes Patient Costs for Males, 65 yrs. old in 2018 |
| AL | $294.29 | $1218.52 | $11,839.24 | $8879.43 | $18,232.40 |
| AK | $499.68 | $2068.98 | $20,102.38 | $15,076.79 | $30,967.37 |
| AZ | $342.04 | $1,416.25 | $13,760.44 | $10,320.33 | $21,191.08 |
| AR | $245.59 | $1016.90 | $9,880.29 | $7,410.22 | $15,215.65 |

APPENDIX

```
USE [HVSMKT]
GO
SET ANSI_NULLS ON
GO
SET QUOTED_IDENTIFIER ON
GO
```

-- ==================================================
-- Author:      HealthView Services
-- Created By: Ron Mastrogiovanni
-- Modified date: 4/30/2009
/*
-- Description: Return Multiple tables with calculation of medical costs based on input paramaters
Call [a_ActuaryTable] procedure and obtain raw data for adjustments
Output tables:
--      Summary costs for first year of retirement and Net Present Value as of retirement year
--      Life Expectancy for client and spouse
--      Average health care cost based on age group
--      Average Total health care cost based on age group
--      Details with discounted values to retirement year (Net Present Value as of retirement year)
--      Annual Detailed Total Costs
--      Planning tools slope calculations Test Proc
exec pHVS_calcHealthCareCostCouple
@CurrentAge=55,@Gender=N'M',@ItemCondition=N'Diabetes: Type II'
,@LifeExpectancy=90,@RetirementAge=65
,@RateofReturnBeforeRetirement=7,@RateofReturninRetirement=5
,@OverrideLifeExpectancy=0,@NPVasofRetirementYear=1
,@CurrentAgeSpouse=50,@GenderSpouse=N'F',@ItemConditionSpouse=N'General Health: Very Good'
,@LifeExpectancySpouse=95,@RetirementAgeSpouse=65

*/

ALTER Procedure [dbo].[pHVS_calcHealthCareCostCouple]
(
    @CurrentAge int
    ,@Gender varchar(1)
    ,@ItemCondition varchar(50)
    ,@LifeExpectancy int
    ,@RetirementAge int =65
    ,@RateofReturnBeforeRetirement float=0.07
    ,@RateofReturninRetirement float=0.05

,@CurrentAgeSpouse int =0
    ,@GenderSpouse varchar(1)=null
    ,@ItemConditionSpouse varchar(50)=null
    ,@LifeExpectancySpouse int=null
    ,@RetirementAgeSpouse int =65
    ,@OverrideLifeExpectancy int =0
    ,@NPVasofRetirementYear int =1
)
as
Begin declare @RateofReturnBeforeRetirementSpouse float
    ,@RateofReturninRetirementSpouse float
Declare @RateofReturn float ,@RateofReturnSpouse float ,@LE1 int
declare @ClientLifeExpectancy decimal(5,1),@SpouseLifeExpectancy decimal(5,1)
 declare @LowerRetirementAge int, @HigherRetirementAge int,
@LowerLifeExpectancy int, @HigherLifeExpectancy int declare @HealthcareCostinRetirement money ,@HealthcareCostFVinRetirement
money,@investmentRequired money,@investmentRequiredin4Years money
    , @HealthcareCostinRetirementSpouse money
,@HealthcareCostFVinRetirementSpouse money,@investmentRequiredSpouse
money,@investmentRequiredin4YearsSpouse money if @RateofReturnBeforeRetirement>=1 set
@RateofReturnBeforeRetirement=@RateofReturnBeforeRetirement/100

```
if @RateofReturninRetirement>=1 set
@RateofReturninRetirement=@RateofReturninRetirement/100

-- Adjust Disease State for High blood Pressurs as == General Health: Moderate
if @ItemCondition='High Blood Pressure'
        set @ItemCondition='General Health: Moderate' if @ItemConditionSpouse='High Blood Pressure'
        set @ItemConditionSpouse='General Health: Moderate'

--Get Client Calculated Life Expectancy
select @ClientLifeExpectancy= CurrentAge +LifeExpectancy
        from ActuaryTable
        where DiseaseState=@ItemCondition
        and Gender=@Gender
        and CurrentAge=@CurrentAge
        and AttainedAge=CurrentAge if @ClientLifeExpectancy is null
        set @ClientLifeExpectancy=0

--Get Spouse Calculated Life Expectancy
select @SpouseLifeExpectancy= CurrentAge +LifeExpectancy
        from ActuaryTable
        where DiseaseState=@ItemConditionSpouse
        and Gender=@GenderSpouse
        and CurrentAge=@CurrentAgeSpouse
        and AttainedAge=CurrentAge if @SpouseLifeExpectancy is null
        set @SpouseLifeExpectancy=0

--Set Life expectancy if requires override
if @OverrideLifeExpectancy=1
        Begin
                set @LifeExpectancy=@ClientLifeExpectancy
                set @LifeExpectancySpouse=@SpouseLifeExpectancy
        End --Declare Output table
declare @Res table(ItemID int identity(1,1)
                                        ,ItemRetID int null
```

```
,ItemCondition varchar(50)
,Gender varchar(1)
,CurrentAge int
,CalculatedYear int
,LifeExpectancy int
,AttainedAge int
,OOP money
,Premuims money
,Dental money
,TotalCost money
,AdjustedOOP money
,AdjustedPremuims money
,AdjustedDental money
,AdjustedTotalCost money
,HealthcareCostinRetirement money
,investmentRequired money
,HealthcareCostinRetirementSpouse money
,investmentRequiredSpouse money
,ClientID varchar(20)null
)
```

```
--Set Default Values for rate of return
    set @RateofReturn=0.06
    set @RateofReturnSpouse=0.06
    set @RateofReturnBeforeRetirement =0.07
    set @RateofReturnBeforeRetirementSpouse=1+@RateofReturnBeforeRetirement
    set @RateofReturninRetirementSpouse=1+@RateofReturninRetirement
    set @RateofReturnBeforeRetirement=1+@RateofReturnBeforeRetirement
    set @RateofReturninRetirement=1+@RateofReturninRetirement
```

```
--get all data for client records to 100
-- use [a_ActuaryTable] stored procedure
insert @Res
    ( ItemCondition
        ,Gender
        ,CurrentAge
        ,CalculatedYear
        ,LifeExpectancy
        ,AttainedAge
        ,OOP
```

```
            ,Premuims
            ,Dental
            ,TotalCost
            ,AdjustedOOP
            ,AdjustedPremuims
            ,AdjustedDental
            ,AdjustedTotalCost
            )
exec [a_ActuaryTable]
@ItemCondition=@ItemCondition
,@Gender=@Gender,@CurrentAge=@CurrentAge,@RateofReturn=@RateofReturn,@LifeExpectancy=100
,@RetirementAge=@RetirementAge update @Res set ClientID='Client' where ClientID is null --get all data for Spouse records to 100
-- use [a_ActuaryTable] stored procedure
if @CurrentAgeSpouse>0
            insert @Res
                (ItemCondition
                ,Gender
                ,CurrentAge
                ,CalculatedYear
                ,LifeExpectancy
                ,AttainedAge
                ,OOP
                ,Premuims
                ,Dental
                ,TotalCost
                ,AdjustedOOP
                ,AdjustedPremuims
                ,AdjustedDental
                ,AdjustedTotalCost )
            exec [a_ActuaryTable]
            @ItemCondition=@ItemConditionSpouse ,@Gender=@GenderSpouse,@CurrentAge=@CurrentAgeSpouse,@RateofReturn=@RateofReturnSpouse,@LifeExpectancy=100
            ,@RetirementAge=@RetirementAgeSpouse update @Res set ClientID='Spouse' where ClientID is null
```

```
--Update ItemRetId used for discoiunting back calculation
update @Res set ItemRetId=AttainedAge-@RetirementAge where ClientID='Client'
update @Res set  HealthcareCostinRetirement=power(@RateofReturninRetirement,-
ItemRetID)*TotalCost where ClientID='Client'
update @Res set
        AdjustedPremuims=power(@RateofReturninRetirement,-ItemRetID)*Premuims
        ,AdjustedOOP=power(@RateofReturninRetirement,-ItemRetID)*OOP
        ,AdjustedDental=power(@RateofReturninRetirement,-ItemRetID)*Dental
where ClientID='Client' update @Res set ItemRetId=AttainedAge-@RetirementAgeSpouse where
ClientID='Spouse'
update @Res set
HealthcareCostinRetirementSpouse=power(@RateofReturninRetirement,-
ItemRetID)*TotalCost where ClientID='Spouse'
update @Res set
        AdjustedPremuims=power(@RateofReturninRetirement,-ItemRetID)*Premuims
        ,AdjustedOOP=power(@RateofReturninRetirement,-ItemRetID)*OOP
        ,AdjustedDental=power(@RateofReturninRetirement,-ItemRetID)*Dental
where ClientID='Spouse' if @NPVasofRetirementYear=1
Begin
        update @Res set  TotalCost= HealthcareCostinRetirement  where
ClientID='Client'
        update @Res set  TotalCost= HealthcareCostinRetirementSpouse where
ClientID='Spouse'
End --Get HealthcareCost in Retirement select
                @HealthcareCostinRetirement=sum(HealthcareCostinRetirement)
                ,@HealthcareCostFVinRetirement=sum(TotalCost)
        from @res
        where
                AttainedAge>=@RetirementAge
                and AttainedAge<=@LifeExpectancy
                and ClientID='Client'
```

```
set @HealthcareCostinRetirementSpouse=0
set @HealthcareCostFVinRetirementSpouse=0 select

@HealthcareCostinRetirementSpouse=sum(HealthcareCostinRetirementSpouse)
        ,@HealthcareCostFVinRetirementSpouse=sum(TotalCost)
from @res
where
        AttainedAge>=@RetirementAge
        and AttainedAge<=@LifeExpectancySpouse
        and ClientID='Spouse' set @investmentRequiredin4Years=0
set @investmentRequiredin4YearsSpouse=0
```

--Adjust Present Value
------------------------
```
select @investmentRequired=power(@RateofReturnBeforeRetirement ,-
(@RetirementAge-@CurrentAge)) *@HealthcareCostinRetirement if @CurrentAgeSpouse>0
        select
@investmentRequiredSpouse=power(@RateofReturnBeforeRetirementSpouse ,-
(@RetirementAgeSpouse-@CurrentAgeSpouse)) *@HealthcareCostinRetirementSpouse if @RetirementAge-@CurrentAge-4>0
        select @investmentRequiredin4Years=power(@RateofReturnBeforeRetirement ,-
(@RetirementAge-@CurrentAge-4)) *@HealthcareCostinRetirement if @CurrentAgeSpouse>0
        begin
        if @RetirementAgeSpouse-@CurrentAgeSpouse-4>0
                select
@investmentRequiredin4YearsSpouse=power(@RateofReturnBeforeRetirementSpouse
,-(@RetirementAgeSpouse-@CurrentAgeSpouse-4))
*@HealthcareCostinRetirementSpouse
        end
```

```
declare @AnnualCost1stYearinRetirementClient money
,@AnnualCost1stYearinRetirementSpouse money set @AnnualCost1stYearinRetirementClient=0
set @AnnualCost1stYearinRetirementSpouse=0 select @AnnualCost1stYearinRetirementClient=TotalCost
        from @Res
        where AttainedAge=@RetirementAge
        and ClientID='Client'
    select @AnnualCost1stYearinRetirementSpouse=TotalCost
        from @Res
        where AttainedAge=@RetirementAgeSpouse
        and ClientID='Spouse' select  @AnnualCost1stYearinRetirementClient as
AnnualCost1stYearinRetirementClient
                ,@AnnualCost1stYearinRetirementSpouse as
AnnualCost1stYearinRetirementSpouse
                ,@HealthcareCostinRetirement as HealthcareCostinRetirement
                ,@investmentRequired as investmentRequired
                ,@HealthcareCostFVinRetirement as
HealthcareCostFVinRetirement
                ,@investmentRequiredin4Years as investmentRequiredin4Years
                ,@HealthcareCostinRetirementSpouse as
HealthcareCostinRetirementSpouse
                ,@investmentRequiredSpouse as investmentRequiredSpouse
                ,@HealthcareCostFVinRetirementSpouse as
HealthcareCostFVinRetirementSpouse
                ,@investmentRequiredin4YearsSpouse as
investmentRequiredin4YearsSpouse
                ,@ClientLifeExpectancy as 'ClientLifeExpectancy'
                ,@SpouseLifeExpectancy as 'SpouseLifeExpectancy' select @LE1=LifeExpectancy
        from @Res
        where ItemCondition=@ItemCondition
```

```
--Remove information beyond life expectancy would apply for Override life
expectancy
        delete from @Res
                where ClientID='Client'
                and AttainedAge>@LifeExpectancy delete from @Res
                where ClientID='Spouse'
                and AttainedAge>@LifeExpectancySpouse ---Create Age Group Result table
        declare @ResGroup table(ItemID int identity(1,1)
                        ,AgeGroup varchar(20)
                        ,AnnualAverageOOPCost money
                        ,AnnualAverageTotalCost money
                        ,AnnualAveragePVOOPCost money
                        ,AnnualAveragePVTotalCost money
                        ,ClientID varchar(20) null
        )

declare @AgeGroup varchar(20),@Interval int,@Interval1 int

--5 Years interval
        set @Interval=5

--Loop to build the table
        declare  @grpYear int,@grpYearInterval int set @grpYear =@CurrentAge set @AgeGroup=''+convert(varchar,@grpYear)

set @grpYear =@RetirementAge
        if @CurrentAgeSpouse=0
         set @LifeExpectancySpouse=@LifeExpectancy declare @LifeExpectancyBoth int
        if @LifeExpectancy>=@LifeExpectancySpouse
                Begin
```

```
            set @LifeExpectancyBoth=@LifeExpectancy
            set @LowerLifeExpectancy=@LifeExpectancySpouse
            set @HigherLifeExpectancy=@LifeExpectancy
        End
    else
        Begin
            set @LifeExpectancyBoth=@LifeExpectancySpouse
            set @LowerLifeExpectancy=@LifeExpectancy
            set @HigherLifeExpectancy=@LifeExpectancySpouse
        End
```

-- Get   Retirement Age and Life expectancy ranges

```
        if @RetirementAge<>@RetirementAgeSpouse and @CurrentAgeSpouse>0
            Begin
                if @RetirementAge>@RetirementAgeSpouse
                    Begin
                        set @LowerRetirementAge=@RetirementAgeSpouse
                        set @HigherRetirementAge=@RetirementAge
                    end
                else
                    Begin
                        set @LowerRetirementAge=@RetirementAge
                        set @HigherRetirementAge=@RetirementAgeSpouse
                    end
            End
        else
            Begin
                set @LowerRetirementAge=@RetirementAge
                set @HigherRetirementAge=@RetirementAge
            end
```

--------------------------------------------------------------------------------

```
print 'Retirement '+ convert(varchar,@LowerRetirementAge)+' -->
'+convert(varchar,@HigherRetirementAge)
print 'LifeExpectancy '+ convert(varchar,@LowerLifeExpectancy)+' -->
'+convert(varchar,@LowerLifeExpectancy)
```

```
if @HigherRetirementAge<65
Begin
        print 'Both are less then 65 '+ '=====
'+convert(varchar,@LowerRetirementAge)+' --> ' +
convert(varchar,@HigherRetirementAge)
        print 'Both are less then 65 '+ '=====
'+convert(varchar,@HigherRetirementAge)+'--> [65] '
End if @HigherRetirementAge=65 if @LowerRetirementAge<65 and @HigherRetirementAge<65 and
@LowerRetirementAge<>@HigherRetirementAge
begin
        print 'Lower is less then 65 to Higer(less then 65)'+ '=====
'+convert(varchar,@LowerRetirementAge)+' --> ' +
convert(varchar,@HigherRetirementAge)
        print 'Both (less then 65) to 65'+'===========
'+convert(varchar,@HigherRetirementAge)+'--> [65] '
end if @LowerRetirementAge<65 and @HigherRetirementAge>=65
begin
        print 'Lower is less then 65 to 65' +'========== '+
convert(varchar,@LowerRetirementAge)+ ' --> [65]' end if @LowerRetirementAge>=65 and @LowerRetirementAge<>@HigherRetirementAge
begin
        print 'Lower is greather or equal to 65 to Higher retirement age'+' ========= '+
convert(varchar,@LowerRetirementAge)+' -->
'+convert(varchar,@HigherRetirementAge)
end --if
-- print 'from Higher Retirement age to  Lower Life Expectancy' +' ======== '+
convert(varchar,@HigherRetirementAge)+' --> '+convert(varchar,
@HigherLifeExpectancy)
--
--
--if @HigherLifeExpectancy>@LowerLifeExpectancy
--begin
```

```
--      print 'from Lower Life Expectancy to Higher Life Expectancy'+' ======== '+
convert(varchar,@LowerLifeExpectancy)+' --> '+convert(varchar,
@HigherLifeExpectancy)
--end
------------------------------------------------------------------------------
------------------------------------------------------------------------------
------------------------------------------------------------------------------

--
if @RetirementAge<>@RetirementAgeSpouse and @CurrentAgeSpouse>0
        Begin
                if @LifeExpectancySpouse>@LifeExpectancy
                        set @LifeExpectancyBoth=@LifeExpectancySpouse if @RetirementAge>@RetirementAgeSpouse
                        Begin
                         set @grpYear =@RetirementAgeSpouse
                         set @grpYearInterval=@RetirementAge-@RetirementAgeSpouse
                        End
                else
                        Begin
                         set @grpYear =@RetirementAge
                         set @grpYearInterval=@RetirementAgeSpouse - @RetirementAge
                        End set @AgeGroup=''+convert(varchar,@grpYear)+'-
'+convert(varchar,@grpYear+@grpYearInterval-1)

insert @resGroup
                        ( ClientID,AgeGroup
                        ,AnnualAverageOOPCost ,AnnualAverageTotalCost
                        ,AnnualAveragePVOOPCost ,AnnualAveragePVTotalCost
                        )
                        select
ClientID,@AgeGroup,avg(OOP),avg(TotalCost),avg(AdjustedOOP),avg(AdjustedTotalCost)
                        from @res
                        where AttainedAge>=@grpYear and
AttainedAge<@grpYear+@grpYearInterval
```

```
                group by ClientID

End if @RetirementAge>=@RetirementAgeSpouse
        set @grpYear =@RetirementAge
else
        set @grpYear =@RetirementAgeSpouse --Calculate information based on interval default 5 years
set @grpYearInterval=5

WHILE @grpYear<=@LifeExpectancyBoth--95
BEGIN
        if @grpYear+@grpYearInterval>=@LifeExpectancyBoth
              begin
                        set @grpYearInterval=@LifeExpectancyBoth-@grpYear+1 end
        set @AgeGroup=''+convert(varchar,@grpYear)+'-
'+convert(varchar,@grpYear+@grpYearInterval-1)
        insert @resGroup
( ClientID,AgeGroup
,AnnualAverageOOPCost ,AnnualAverageTotalCost
,AnnualAveragePVOOPCost ,AnnualAveragePVTotalCost
)
        select
                ClientID,@AgeGroup
                ,avg(OOP)
                ,avg(TotalCost)
                ,avg(AdjustedOOP)
                ,avg(AdjustedTotalCost)
        from @res
        where AttainedAge>=@grpYear
                and AttainedAge<@grpYear+@grpYearInterval
   group by ClientID if @grpYear>=@LifeExpectancyBoth
                BREAK
``` set @grpYear =@grpYear+@grpYearInterval

END insert @ResGroup(ClientID,AgeGroup,AnnualAverageTotalCost)
select 'Client',B.AgeGroup,0
    from (select ClientID,AgeGroup,AnnualAverageTotalCost from @ResGroup where ClientId='Client') A
        right Outer join (select ClientID,AgeGroup,AnnualAverageTotalCost from @ResGroup where ClientId='Spouse') B
        on A.AgeGroup=B.AgeGroup
        where A.ClientID is null insert @ResGroup(ClientID,AgeGroup,AnnualAverageTotalCost)
select 'Spouse',A.AgeGroup,0
    from (select ClientID,AgeGroup,AnnualAverageTotalCost from @ResGroup where ClientId='Client') A
        left Outer join (select ClientID,AgeGroup,AnnualAverageTotalCost from @ResGroup where ClientId='Spouse') B
        on A.AgeGroup=B.AgeGroup
        where B.ClientID is null --Result Table 2
select ClientID,AgeGroup,AnnualAverageTotalCost from @ResGroup
order by AgeGroup,ClientId --Result Table 3
select AgeGroup,sum(AnnualAverageTotalCost) as 'AnnualAverageTotalCost' from @ResGroup
group by AgeGroup --Result Table 4
select ClientID,ItemID,ItemRetID, ItemCondition,gender
,currentage,CalculatedYear,LifeExpectancy,AttainedAge,TotalCost
,Premuims ,HealthcareCostinRetirement,HealthcareCostinRetirementSpouse
,OOP,Dental

```
,AdjustedPremuims,AdjustedOOP,AdjustedDental
from @Res
where attainedage <=@LifeExpectancy
order by ClientID,ItemCondition,Gender,AttainedAge declare @OOP table(
                                Age int
                                ,TotalCostClient money
                                ,TotalCostSpouse money
                                ,TotalCost money

)

insert @OOP (age, TotalCostClient)
        select AttainedAge,TotalCost
                From @res
                Where ClientID='Client'
                Order by AttainedAge insert @OOP (age, TotalCostSpouse)
        select r.AttainedAge,r.TotalCost
                From @res R
                Where r.ClientID='Spouse'
                and AttainedAge not in (select Age from @OOP)

update @OOP
        Set TotalCostSpouse=r.totalCost
        from @Res r inner Join @oop o on r.AttainedAge=o.Age and r.clientid='Spouse' update @OOP Set TotalCostClient=0 where TotalCostClient is null
        update @OOP Set TotalCostSpouse=0 where TotalCostSpouse is null
        if @CurrentAgeSpouse=0
                update @OOP Set TotalCostSpouse=0

Update @OOP set TotalCost=TotalCostClient+TotalCostSpouse
```

--Result Table 5 select * from @OOP order by Age

----Planning Tool results Plan declare @OP table(
    Age int
    ,TotalCost money
    ,Change decimal(8,4)
    ,Amount money
    ,AnnualIncrease decimal(8,4)
    )

declare @OPSpouse table(
    Age int
    ,TotalCost money
    ,Change decimal(8,4)
    ,Amount money
    ,AnnualIncrease decimal(8,4)
    )

declare @ORes table(
    BeginningAge int
    ,Amount money
    ,AnnualIncrease decimal(8,4)
    )

declare @OResSpouse table(
    BeginningAge int
    ,Amount money
    ,AnnualIncrease decimal(8,4)
    )

insert @OP (Age,TotalCost,Change)
    select o2.age,o2.totalcostClient
    , case o1.totalcostClient when 0 then 0 else (o2.totalcostClient/o1.totalcostClient)-1 end
    from @OOP o1 inner join @oop o2

```
    on (o1.age+1)= o2.age
    order by o1.Age insert @OPSpouse (Age,TotalCost,Change)
    select o2.age,o2.totalcostSpouse
    , case o1.totalcostSpouse when 0 then 0 else
(o2.totalcostSpouse/o1.totalcostSpouse)-1 end
    from @OOP o1 inner join @oop o2
    on (o1.age+1)= o2.age
    order by o1.Age insert @ORes (BeginningAge,Amount )
    select  age, totalcostClient  from @OOP
    where  Age =@CurrentAge if @CurrentAgeSpouse>0
    insert @OResSpouse (BeginningAge,Amount )
        select  age, totalcostSpouse  from @OOP
        where  Age =@CurrentAgeSpouse insert @ORes (BeginningAge, Amount )
    select  age, totalcostClient  from @OOP
    where  Age =65 if @CurrentAgeSpouse>0
    insert @OResSpouse (BeginningAge, Amount )
        select  age, totalcostSpouse  from @OOP
        where  Age =65 if @RetirementAge<> 65
    insert @ORes (BeginningAge, Amount )
    select  age, totalcostClient  from @OOP
    where  Age  =@RetirementAge if @CurrentAgeSpouse>0
    if @RetirementAgeSpouse<> 65
        insert @OResSpouse (BeginningAge, Amount )
        select  age, totalcostSpouse  from @OOP
        where  Age  =@RetirementAgeSpouse
```

```
declare @change decimal(8,4),@Amount money,@i int
declare @changeSpouse decimal(8,4),@AmountSpouse money,@iSpouse int /*Begining Age*/
        --Get the average of the change and the TotalCost at current Age
        -- to either 65 or Retirement age less then 65
        select @change= avg(change) from @OP
                where age<@RetirementAge
                    and age <65
        select @Amount=Amount from @ORes where BeginningAge=@CurrentAge select @changeSpouse= avg(change) from @OPSpouse
                where age<@RetirementAgeSpouse
                    and age <65
        select @AmountSpouse=Amount from @OResSpouse where
BeginningAge=@CurrentAgeSpouse --Update Output table with increate and amount
        update @Ores
                set AnnualIncrease =@change
                ,Amount=@Amount
        where BeginningAge=@CurrentAge --Update Output table with increate and amount
        update @OresSpouse
                set AnnualIncrease =@changeSpouse
                ,Amount=@AmountSpouse
        where BeginningAge=@CurrentAgeSpouse -----------------------------------
        --Update original table with running costs
        -- Up to Retirement Age
        update @OP
                set AnnualIncrease =1+@change
                    ,Amount=@Amount*power(1+@change,age-@CurrentAge)
        where age >=@CurrentAge
    and age<@RetirementAge
        and age <65
-----------------------------------
        --Update original table with running costs
```

```
    -- Up to Retirement Age
    update @OPSpouse
            set AnnualIncrease =1+@changeSpouse
                    ,Amount=@AmountSpouse*power(1+@changeSpouse,age-@CurrentAgeSpouse)
            where age >=@CurrentAgeSpouse
    and age<@RetirementAgeSpouse
        and age <65

/*Retirement Age <65 to 65*/
------------------------
        --Get the average of the change and the TotalCost at current Age
        select @change= avg(change) from @OP
                where age>@RetirementAge
                and age<65
        select @Amount=Amount from @ORes where BeginningAge=@RetirementAge --Get the average of the change and the TotalCost at current Age
        select @changeSpouse= avg(change) from @OPSpouse
                where age>@RetirementAgeSpouse
                and age<65
        select @AmountSpouse=Amount from @OResSpouse where
BeginningAge=@RetirementAgeSpouse --Update Output table with increate and amount
        update @Ores
                set AnnualIncrease =@change
                        ,Amount=@Amount
        where BeginningAge =@RetirementAge --Update Output table with increate and amount
        update @OresSpouse
                set AnnualIncrease =@changeSpouse
                        ,Amount=@AmountSpouse
        where BeginningAge =@RetirementAgeSpouse ----------------------------------
        --Update original table with running costs
        update @OP
                set AnnualIncrease =1+@change
                        ,Amount=@Amount*power(1+@change,age-@RetirementAge)
```

```
        where age >=@RetirementAge
   and age<65
       --Update original table with running costs
       update @OPSpouse
              set AnnualIncrease =1+@changeSpouse
                     ,Amount=@AmountSpouse*power(1+@changeSpouse,age-
@RetirementAgeSpouse)
       where age >=@RetirementAgeSpouse
   and age<65
-----------------
/*Retirement Age > 65 --> 65 to Retirement Age*/
       --Get the average of the change and the TotalCost at current Age
       select @change= avg(change) from @OP
              where age>65
              and age<@RetirementAge
       select @Amount=Amount from @ORes where BeginningAge=65

--Get the average of the change and the TotalCost at current Age
       select @changeSpouse= avg(change) from @OPSpouse
              where age>65
              and age<@RetirementAgeSpouse
       select @AmountSpouse=Amount from @OResSpouse where BeginningAge=65

--Update Output table with increate and amount
       update @Ores
              set AnnualIncrease =@change
              ,Amount=@Amount
       where BeginningAge=65 update @OresSpouse
              set AnnualIncrease =@changeSpouse
              ,Amount=@AmountSpouse
       where BeginningAge=65

----------------------------------
       --Update original table with running costs
       -- Up to Retirement Age
       update @OP
              set AnnualIncrease =1+@change
```

```
                    ,Amount=@Amount*power(1+@change,age-65)
    where age >=65
and age<@RetirementAge update @OPSpouse
        set AnnualIncrease =1+@changeSpouse
                ,Amount=@AmountSpouse*power(1+@changeSpouse,age-65)
    where age >=65
and age<@RetirementAgeSpouse
```

/*Retirement Age > 65 --> Retirement Age to Life Expectancy*/

```
    --Get the average of the change and the TotalCost at current Age
    select @change= avg(change) from @OP
        where age>65
        and age>@RetirementAge
and age <=@LifeExpectancy
    select @Amount=Amount,@i=BeginningAge from @ORes where
BeginningAge=@RetirementAge and BeginningAge>=65

--Get the average of the change and the TotalCost at current Age
    select @changeSpouse= avg(change) from @OPSpouse
        where age>65
        and age>@RetirementAgeSpouse
and age <=@LifeExpectancySpouse
    select @AmountSpouse=Amount,@iSpouse=BeginningAge from @OResSpouse
where BeginningAge=@RetirementAgeSpouse and BeginningAge>=65

--Update Output table with increate and amount
    update @Ores
        set AnnualIncrease =@change
        ,Amount=@Amount
    where BeginningAge>=@RetirementAge
    and BeginningAge>=65

--Update Output table with increate and amount
```

```
update @OresSpouse
        set AnnualIncrease =@changeSpouse
        ,Amount=@AmountSpouse
    where BeginningAge>=@RetirementAgeSpouse
    and BeginningAge>=65
```

---------------------------------

```
    --Update original table with running costs
    -- Up to Retirement Age
    update @OP
        set AnnualIncrease =1+@change
                ,Amount=@Amount*power(1+@change,age-@i)
    where age >=65
    and age>@RetirementAge update @OPSpouse
        set AnnualIncrease =1+@changeSpouse
                ,Amount=@AmountSpouse*power(1+@changeSpouse,age-@i)
    where age >=65
    and age>@RetirementAgeSpouse
```

```
--Planning tools result table Client
select
        BeginningAge as 'Year'
        ,case when BeginningAge=@CurrentAge then 'Today '
        when BeginningAge=@RetirementAge then 'Retirement '
        else 'Special Year ' end as 'Beginning'
        ,Amount,AnnualIncrease as 'Annual Increase'
        ,case when BeginningAge=@CurrentAge then 'Present Value' else 'Future Value'
end as ' '
from @ORes
        order by BeginningAge --Planning tools result table Spouse
select
        BeginningAge as 'Year'
        ,case when BeginningAge=@CurrentAgeSpouse then 'Today '
        when BeginningAge=@RetirementAgeSpouse then 'Retirement '
        else 'Special Year ' end as 'Beginning'
        ,Amount,AnnualIncrease as 'Annual Increase'
        ,case when BeginningAge=@CurrentAgeSpouse then 'Present Value' else 'Future
Value' end as ' '
from @OResSpouse
```

```
            order by BeginningAge insert @OP (age,totalcost,change,Amount,AnnualIncrease)
select BeginningAge,Amount,AnnualIncrease,Amount,AnnualIncrease
from @Ores
where BeginningAge=@CurrentAge update @OP
set AnnualIncrease=or1.AnnualIncrease
,Amount=or1.Amount
from @OP o inner Join @ORes or1
on o.Age=or1.BeginningAge -- All output data
select * from @OP
order by age -- All output data
select '=',o1.Age,o1.TotalCost,o1.Change,o1.Amount,o1.AnnualIncrease
,'=',o2.Age,o2.TotalCost,o2.Change,o2.Amount,o2.AnnualIncrease
,isnull(o2.AnnualIncrease,o2.Change)
from @OP o1 inner join @OP o2
on (o1.age)= (o2.age +1)
order by o1.Age
select * from @OP -- All output data  Life expectancy
select @CurrentAge,@RetirementAge,@LifeExpectancy End
```

```
USE [HVSMKT]
GO
 SET ANSI_NULLS ON
GO
SET QUOTED_IDENTIFIER ON
GO
```

-- ================================================
-- Author:      Shalom Keynan
-- Created By: Shalom Keynan
-- Modified date: 4/30/2009
/*
-- Description: Return Future value based on disease state gender and age
-- from current age to 100 Parent procedure will handale present values and retirement period.

Called By pHVS_calcHealthCareCostCouple
Output:
-- Future value of acturay tables Test Proc
exec a_ActuaryTable
@ItemCondition=N'Diabetes: Type II',@Gender=N'M',@CurrentAge=55
,@LifeExpectancy=90,@RetirementAge=65

*/

ALTER PROCEDURE [dbo].[a_ActuaryTable]
        -- Parameters for the stored procedure
 @ItemCondition varchar(50)
,@Gender varchar(1)
,@CurrentAge int ,@LifeExpectancy int =100
,@RateofReturn float=0.06
,@RetirementAge int=0
,@HaelthContributionRatio float=0.25

AS
BEGIN

```
declare @HCHBStatus varchar(50),@LifeSpan int , @CalculatedLifeExpectancy int
set @HCHBStatus=''

--Get Item Condition to resolve scenarios where it is High Blood Pressure
set @HCHBStatus=@ItemCondition --Adjust special healthCondition for Cholesterol & blood pressure
if @ItemCondition='High Cholesterol'
Begin
        set @HCHBStatus='High Cholesterol'
End if @ItemCondition='High Cholesterol High Blood Pressure'
Begin
                set @HCHBStatus='High Cholesterol High Blood Pressure'
                set @ItemCondition='General Health: Moderate'
End
if @ItemCondition='High Blood Pressure'
Begin
                set @HCHBStatus='High Blood Pressure'
                set @ItemCondition='General Health: Moderate'
End declare @Res table(ItemID int identity(1,1)
,CalculatedYear int
        ,ItemCondition varchar(50)
        ,Gender varchar(1)
        ,CurrentAge int
        ,AttainedAge int
        ,OOP money
        ,Premiums money
        ,Dental money
        ,TotalCost money ,WOOP money
        ,WPremiums money
        ,WDental money
        ,WTotalCost money ,ROOP money
        ,RPremiums money
```

```
,RDental money
,RTotalCost money

,AdjustedOOP money
,AdjustedPremiums money
,AdjustedDental money
,AdjustedTotalCost money
,LifeExpectancy int
)

insert @res(CalculatedYear  ,ItemCondition    ,Gender    ,CurrentAge
       ,AttainedAge
,OOP       ,Premiums    ,Dental    ,TotalCost
    ,WOOP    ,WPremiums  ,WDental ,WTotalCost  ,ROOP    ,RPremiums
    ,RDental,RTotalCost ,AdjustedOOP     ,AdjustedPremiums  ,AdjustedDental
    ,AdjustedTotalCost,LifeExpectancy)
    SELECT    [Year] as 'CalculatedYear',  DiseaseState as 'ItemCondition', Gender,
CurrentAge, AttainedAge
    ,0 ,0 , 0, 0
    , WorkingOOP+WorkingVision+WorkingHearing+DentalOOP as 'WOOP',
WorkingPremiums as 'WPremiums',DentalPremiums as 'WDental'
    ,0  as 'WTotalCost'-- WorkingOOP+WorkingVision+WorkingHearing+DentalOOP +
WorkingPremiums +DentalPremiums ,RetiredOOP +RetiredVision +RetiredHearing +DentalOOP as 'ROOP',RetiredPremiums
as 'RPremiums', DentalPremiums  as 'RDental'
,0 as 'RTotalCost'--RetiredOOP +RetiredVision +RetiredHearing +DentalOOP
+RetiredPremiums+ DentalPremiums ,0 ,0 , 0, 0 ,CurrentAge+LifeExpectancy
        FROM    dbo.ActuaryTable where DiseaseState=@ItemCondition
    and Gender=@Gender
    and CurrentAge=@CurrentAge -- Employee works from current age to Retirement year
        update @Res
```

```
                set
oop=woop,Premiums=WPremiums*(@HaelthContributionRatio),Dental=Wdental*(@Ha
elthContributionRatio)
                ,
TotalCost=WOOP+WPremiums*(@HaelthContributionRatio)+Wdental*(@HaelthContri
butionRatio)
                where attainedAge<@RetirementAge if  @RetirementAge<65
        Begin
                --Before 65

-- Employee responsible for healthcare cost from retirement year to age 64
(retirement year is 65)
                update @Res
                set oop=woop,Premiums=WPremiums,Dental=Wdental
                , TotalCost=WOOP+WPremiums+Wdental
                where attainedAge>=@RetirementAge and @RetirementAge<65

--Use retirement numbers from age 65
                update @Res
                set oop=Roop,Premiums=RPremiums,Dental=Rdental
                , TotalCost=ROOP+RPremiums+Rdental
                where attainedAge>=65 --and @RetirementAge>=65

End if @RetirementAge>=65
        Begin

--Use retirement numbers
                update @Res
                set oop=Roop,Premiums=RPremiums,Dental=Rdental
                , TotalCost=ROOP+RPremiums+Rdental
                where attainedAge>=@RetirementAge --and @RetirementAge>=65
        End
```

```
select
ItemCondition as 'ItemCondition',    Gender,      CurrentAge, CalculatedYear as
'CalculatedYear', LifeExpectancy,   AttainedAge,   OOP,       Premiums,    Dental
,        TotalCost,     0 as AdjustedOOP,    0 as AdjustedPremiums,0 as
         AdjustedDental,      0 as AdjustedTotalCost FROM     @Res where ItemCondition=@ItemCondition
and Gender=@Gender
and CurrentAge=@CurrentAge End
```

What is claimed is:

1. A system for determining projected retirement healthcare expenses for at least one client, comprising:
 a processor;
 a network connection; and
 a non-transitory, computer-readable storage medium in operable communication with the processor, wherein the computer-readable storage medium contains one or more programming instructions that, when executed, cause the processor to:
 receive, from a client device, client information related to the client and any current client partner, comprising basic characteristics, lifestyle characteristics, and medical history characteristics,
 access, from at least one actual claims database, actual claims information comprising more than 50,000,000 records of actual insurance claims and costs for resolving the actual insurance claims,
 access, from at least one database, actuarial data,
 calculate a life expectancy value and a plurality of base healthcare expense cost values based on the client information, the actuarial data, and the actual claims information, wherein each of the plurality of base healthcare expense cost values are configured to indicate a cost of a healthcare expense during retirement,
 calculate a plurality of cost adjustment factors based on the actual claims information, the plurality of cost adjustment factors comprising a condition diagnosis duration factor, a condition management regime factor, a cost trend factor, a client age factor, and a client gender factor, each of the plurality of cost adjustment factors being configured to predict a future cost for the plurality of base healthcare expense cost values and to be statistically reliable by being tested using a minimum of about 2,000 actual claims;
 calculate a medical expenses retirement savings value and a plurality of adjusted healthcare cost values based on the life expectancy value, the plurality of base healthcare expense cost values, and the plurality of cost adjustment values,
 receive updated information comprising at least one of a legislative change and a cost trend change;
 dynamically modify the plurality of adjusted healthcare cost values based on the updated information;
 display each of the plurality of adjusted healthcare costs values in a cell, wherein the plurality of adjusted healthcare costs cells are arranged in at least one row and at least one column, wherein the at least one column is associated with a type of healthcare expense and the at least one row is associated with the client information and a level of healthcare management;
 responsive to receiving user input identifying a specific cell, display a plurality of costs based on each of the plurality of cost adjustment factors associated with the adjusted healthcare cost in the specific cell;
 generate, based on the medical expenses retirement savings value and the plurality of adjusted healthcare cost values, a financial results report, and
 transmit, via the network connection, the financial results report and the medical expenses report comprising the medical expenses retirement savings value, the plurality of base healthcare expense cost values, and the plurality of adjusted healthcare cost values to the client computing device.

2. The system of claim 1, wherein the plurality of base healthcare expense cost values comprise an individual medical expense, an individual prescription expense, a dental expense, a hearing expense, a vision expense, in-hospital expenses, and in-hospital prescription expenses.

3. The system of claim 2, wherein the plurality of base healthcare expense cost values comprise an employer-based medical expense and an employer-based prescription expense.

4. A non-transitory computer-readable storage medium having computer-readable program code configured to determine projected retirement healthcare expenses, the computer-readable program code comprising:
 computer-readable program code configured to receive, from a client device, client information related to the client and any current client partner, comprising basic characteristics, lifestyle characteristics, and medical history characteristics;
 computer-readable program code configured to access, from at least one actual claims database, actual claims information comprising more than 50,000,000 records of actual insurance claims and costs for resolving the actual insurance claims;
 computer-readable program code configured to access, from at least one database, actuarial data;
 computer-readable program code configured to calculate a life expectancy value and a plurality of base healthcare expense cost values based on the client information, the actuarial data, and the actual claims information, wherein each of the plurality of base healthcare expense cost values are configured to indicate a cost of a healthcare expense during retirement;
 computer-readable program code configured to calculate a plurality of cost adjustment factors based on the actual claims information, the plurality of cost adjustment factors comprising a condition diagnosis duration factor, a condition management regime factor, a cost trend factor, a client age factor, and a client gender factor, each of the plurality of cost adjustment factors being configured to predict a future cost for the plurality of base healthcare expense cost values and to be statistically reliable by being tested using a minimum of about 2,000 actual claims;
 computer-readable program code configured to calculate a medical expenses retirement savings value and a plurality of adjusted healthcare cost values based on the life expectancy value, the plurality of base healthcare expense cost values, and the plurality of cost adjustment factors;
 computer-readable program code configured to receive updated information comprising at least one of a legislative change and a cost trend change;
 computer-readable program code configured to dynamically modify the plurality of adjusted healthcare cost values based on the updated information;
 computer-readable program code configured to display each of the plurality of adjusted healthcare costs values in a cell, wherein the plurality of adjusted healthcare costs cells are arranged in at least one row and at least one column, wherein the at least one column is associated with a type of healthcare expense and the at least one row is associated with the client information and a level of healthcare management;
 computer-readable program code configured to responsive to receiving user input identifying a specific cell, display a plurality of costs based on each of the plurality of cost adjustment factors associated with the adjusted healthcare cost in the specific cell; and
 computer-readable program code configured to transmit, via a network connection, the financial results report and the medical expenses report comprising the medical expenses retirement savings value, the plurality of base healthcare expense cost values, and the plurality of adjusted healthcare cost values to the client computing device.

5. The non-transitory computer-readable storage medium of claim 4, wherein the plurality of base healthcare expense cost values comprise an individual medical expense, an individual prescription expense, a dental expense, a hearing expense, a vision expense, in-hospital expenses, and in-hospital prescription expenses.

6. The non-transitory computer-readable storage medium of claim 5, wherein the plurality of base healthcare expense cost values comprise an employer-based medical expense and an employer-based prescription expense.

7. The system of claim 1, wherein the computer-readable storage medium further contains one or more programming instructions that, when executed, cause the processor to:
receive updated information comprising a cost trend change; and update the cost adjustment factors based on the updated information.

8. The system of claim 4, wherein the computer-readable storage medium further contains one or more programming instructions that, when executed, cause the processor to:
receive updated information comprising a cost trend change; and
update the cost adjustment factors based on the updated information.

9. The system of claim 1, wherein the computer-readable storage medium further contains one or more programming instructions that, when executed, cause the processor to:
access a stored input parameter of a rate of return before retirement,
access a stored input parameter of a rate of return during retirement,
access the input flag of whether the calculation should be made using net present value or present value as of a retirement year.

10. The non-transitory computer-readable storage medium of claim 4, further comprising one or more programming instructions that, when executed, cause the processor to:
access a stored input parameter of a rate of return before retirement,
access a stored input parameter of a rate of return during retirement,
access the input flag of whether the calculation should be made using net present value or present value as of a retirement year.

* * * * *